(12) United States Patent
Savarese et al.

(10) Patent No.: US 11,614,453 B1
(45) Date of Patent: Mar. 28, 2023

(54) DEVICE OF DISTRIBUTION OF IMPREGNATED SUPPORTS AND ASSOCIATED METHOD

(71) Applicant: COPAN ITALIA S.p.A., Brescia (IT)

(72) Inventors: Mario Savarese, Brescia (IT); Salvatore Balzano, Brescia (IT); Laura Navarria, Brescia (IT); Guido Schinetti, Brescia (IT); Andrea Bonatti, Brescia (IT)

(73) Assignee: Copan Italia S.p.A., Brescia (IT)

( * ) Notice: Subject to any disclaimer, the term of this patent is extended or adjusted under 35 U.S.C. 154(b) by 0 days.

(21) Appl. No.: 17/457,549

(22) Filed: Dec. 3, 2021

(30) Foreign Application Priority Data

Sep. 28, 2021 (IT) .......................... 102021000024827

(51) Int. Cl.
| | |
|---|---|
| G06F 17/00 | (2019.01) |
| G01N 35/00 | (2006.01) |
| G01N 35/02 | (2006.01) |
| C12M 1/00 | (2006.01) |
| C12Q 1/18 | (2006.01) |
| G01N 35/04 | (2006.01) |

(52) U.S. Cl.
CPC .......... *G01N 35/025* (2013.01); *C12M 99/02* (2013.01); *C12Q 1/18* (2013.01); *G01N 2035/0444* (2013.01)

(58) Field of Classification Search
None
See application file for complete search history.

(56) References Cited

U.S. PATENT DOCUMENTS 2,865,156 A * 12/1958 Wolfson ................. C12M 99/00
  53/237
4,215,799 A *  8/1980 Swaine .............. G01N 35/1002
  221/211

(Continued)

FOREIGN PATENT DOCUMENTS

| EP | 2518136 | 6/2017 |
| GB | 2001432 | 1/1979 |

OTHER PUBLICATIONS

U.S. Appl. No. 17/457,552, filed Dec. 3, 2021, Savarese et al.

(Continued)

*Primary Examiner* — P. Kathryn Wright
(74) *Attorney, Agent, or Firm* — Fish & Richardson P.C.

(57) ABSTRACT

A method for distribution of supports impregnated with antibiotics includes a step of positioning of a plurality of tubular containers, each one containing a plurality of supports impregnated with antibiotics and stacked, in a corresponding plurality of seats of a dispenser. Extraction of at least a first support from a first container is performed using an extractor, the step of extraction being performed in correspondence of an upper end of the first container and comprising a movement of the first support between a first position inside of the first container and a second position extracted from the first container, said first position and said second position lying substantially in correspondence of an upper surface of the dispenser. Collection of the first support from the second position is performed using a collector. Transportation of the first support towards a culture plate by the collector is performed.

22 Claims, 10 Drawing Sheets

(56) References Cited

U.S. PATENT DOCUMENTS 5,377,865 A * 1/1995 Thomson ............... C12M 99/00
221/93
2012/0277905 A1* 11/2012 Botma ................... C12M 41/48
700/243

OTHER PUBLICATIONS

U.S. Appl. No. 17/457,555, filed Dec. 3, 2021, Savarese et al.
IT Office Action issued in Italian Appln. No. 102021000024827, dated May 25, 2022, 10 pages.

* cited by examiner

DEVICE OF DISTRIBUTION OF IMPREGNATED SUPPORTS AND ASSOCIATED METHOD

CROSS-REFERENCE TO RELATED APPLICATION(S)

This application claims the benefit of priority to Italian Application No. 102021000024827, filed Sep. 28, 2021, the contents of which are hereby incorporated by reference.

TECHNICAL FIELD

The present disclosure refers to the field of automatic machines, and in detail concerns a method and a device of distribution of impregnated supports.

The present disclosure concerns also a computer program designed to cause the execution of the method of distribution of impregnated supports.

The present disclosure concerns also a use of the device of distribution of impregnated supports for performing antibiotic sensitivity tests.

BACKGROUND

From prior art dispensing devices of impregnated discs are known, for example impregnated with antibiotics, configured for moving said discs from a dispenser toward a culture plate. These dispensing devices are mainly designed to perform antibiotic sensitivity tests (typically shortened with the acronym AST).

An example of this dispensing device is described in the document EP 2 518 136 B1. This document discloses a particular type of dispensing device comprising a magazine for containers of impregnated discs, able to rotate, which has a shape of circular charger. This magazine comprises a lateral wall in correspondence of which there is a plurality of openings able to allow the extraction of said impregnated discs.

Drawer-like moving means are movable in a radially external direction from a radially-internal position of the magazine to move, each one thereof, a disc impregnated from a bottom portion of a container to an extraction position along said radially external direction.

In EP 2 518 136, the movement of impregnated discs through the device described in the document is slowed down by the presence of drawer-like moving means that come out from the lateral wall of the magazine, to bring the impregnated discs to the extraction position outside of the magazine itself.

The Applicant notes that the presence of drawer-like moving means strongly limits the speed at which it is possible to activate the dispensing device described in EP 2 518 136. These drawer-like moving means, also due to their position substantially internal to the magazine, are complex and need complex mechanical actuators that can compromise the reliability of the dispensing device.

The purpose of the present disclosure is to describe a device and a method able to solve the aforementioned drawbacks.

The purpose of the present disclosure is also to describe a program for computer that allows to solve the aforementioned drawbacks.

SUMMARY

In order to solve the drawbacks of the devices of known art, the Applicant has conceived a method and a device of distribution of supports (30) of improved type, which allow to speed up and/or make the extraction of impregnated supports (30) from a plurality of containers (20) arranged on a dispenser (10) easier.

The present summary shows the object of the present disclosure in some of its salient aspects, which can be combined among them or with portions of the following detailed description.

[Method]

According to the present disclosure, it is herein described a method of distribution of supports (30) impregnated with antibiotics, comprising:
- a step (1000) of positioning of a plurality of tubular containers (20), each one containing a plurality of supports (30) impregnated with antibiotics and stacked, in a corresponding plurality of seats (11) of a dispenser (10),
- a first step of extraction (1001) of at least a first support (30) from a first container (20), by means of an extractor (18), the step of extraction (1001) being performed in correspondence of an upper end of the first container (20) and comprising a movement (1002) of the first support (30) between a first position (16) inside the first container (20) and a second position (17) extracted from the first container, said first position (16) and said second position (17) lying substantially in correspondence of an upper surface of the dispenser (10) and/or of a same horizontal plane;
- a step of collection of the first support (30) from the second position (17) by means of a collector (19),
- a step of transportation (1004) of the first support (30) towards a culture plate (40) by means of the collector (19).

According to the present disclosure is also described a method of distribution of supports (30), comprising:
- a step (1000) of positioning of a plurality of containers (20), each one containing a plurality of supports (30) stacked, in a corresponding plurality of seats (11) of a dispenser (10),
- a first step of extraction (1001) of at least a first support (30) from a first container (20), by means of an extractor (18), the step of extraction (1001) comprising a movement (1002) of the first support (30) between a first position (16) within the first container (20) and a second position (17) extracted from the first container,
- a step of collection of the first support (30) from the second position (17) by means of a collector (19),
- a step of transportation (1004) of the first support (30) towards a culture plate (40) by means of the collector (19).

According to another non-limiting aspect, the method comprises a step of deposition of the first support (30) on the culture plate (40).

According to another non-limiting aspect, the step of extraction (1001) is performed in correspondence of an upper end of the first container (20).

According to another non-limiting aspect, the step of extraction (1001) is performed in correspondence of a lower end of the first container (20).

According to another non-limiting aspect, the step of deposition of the first support (30) on the culture plate (40) is performed by the collector (19).

According to another non-limiting aspect, said first position (16) and said second position (17) lie substantially in correspondence of an upper surface of the dispenser (10) and/or of a same horizontal plane.

According to another non-limiting aspect, said first position (16) and said second position (17) lie in substantial correspondence of a surface of the dispenser (10) accessible from above.

According to another non-limiting aspect, the supports (30) are supports configured and destined to be impregnated with medical substances, or are supports impregnated with medical substances.

According to another non-limiting aspect, the supports (30) are impregnated with antibiotics.

According to another non-limiting aspect, said medical substances comprise antibiotics.

According to another non-limiting aspect, the method comprises at least a second step of extraction (1001) of at least a first support (30) from a second container (20), by means of the extractor (18), and a step of relative movement between the extractor (18) and the dispenser (10) performed between said first step of extraction (1001) and said second step of extraction (1001), or at least a plurality of steps of extraction (1001) of a plurality of first supports (30) from a corresponding plurality of containers (20), by means of the extractor (18), and a plurality of steps of relative movement between the extractor (18) and the dispenser (10) performed each one between two of said steps of extraction (1001).

According to another non-limiting aspect, the step of movement (1002) comprises a rotation and/or a translation of the extractor (18) with respect to the dispenser (10) and/or comprises a rotation and/or a translation of the dispenser (10) with respect to the extractor.

According to another non-limiting aspect, the method comprises a step of positioning of the dispenser (10) in an operating position in correspondence of which a first seat (11) of said plurality of seats (11) is in a predefined position of extraction configured and designed to allow the extraction of the at least a first support (30) from an upper end of the first container (20) housed in said first seat (11), by means of the extractor (18), and/or the movement (1002) of the at least a first support (30) takes place starting from an upper end of the first container (20) and wherein an upper end of the first container (20) is in substantial correspondence of the first position (16), optionally said predefined position of extraction being designed to allow the extraction of the at least a first support (30) from a supports unloading portion (20s) of the first container (20), in particular from an end of supports (30) unloading of the first container (20) directed upwards and substantially facing itself on the upper surface of the dispenser (10).

According to another non-limiting aspect, the step of rotation and/or translation of the dispenser (10) comprises a step of controlled rotation (1007) of the dispenser (10) through a rotor, optionally automatically controlled, so that a second seat (11) of said plurality of seats (11) of the dispenser (10) be in said predefined position of extraction configured and designed to allow the extraction of the at least a first support (30) from an upper end of a second container (20) housed in said second seat (11), by means of the extractor (18).

According to another non-limiting aspect, the dispenser (10) has a configuration at least partially circular and the seats (11) are arranged according to an arrangement substantially circular in the dispenser (10).

According to another non-limiting aspect, the dispenser (10) performs the steps of movement between the positions of extraction through rotation, and/or the movement (1002) of the first support (30) between the first position (16) and the second position (17) comprises a translation along a direction substantially radial with respect to a centre of the dispenser (10), optionally said movement (1002) comprising a translation along a direction radially external with respect to the centre of the dispenser (10) or comprising a translation along a direction radially internal with respect to the centre of the dispenser (10).

According to another non-limiting aspect, the method comprises a step of holding of the at least a first support (30) at least at the end of the step of extraction (1001), in substantial correspondence of the second position (17) and/or during the step of collection and/or of transportation (1004) through the collector (19), said step of holding comprising the creation of a vacuum between the first support (30) and a striking surface by means of at least a first vacuum holder (14v).

According to another non-limiting aspect, the method comprises a step of holding of the at least a first support (30) at least before the step of transportation (1004) said step of holding comprising the creation of a vacuum between the first support (30) and a striking surface by means of at least a first vacuum holder (14v).

According to another non-limiting aspect, said striking surface is at least one between an upper surface of the dispenser (10), or a surface of the dispenser (10) accessible from above, or is a surface in substantial correspondence of a collection area of an auxiliary dispenser (10w) configured for housing a plurality of supports (30) in a respective plurality of collection areas (10r').

According to another non-limiting aspect, the method comprises a step of holding of the first support (30) of the first container (20) by means of the creation of a vacuum between said upper surface of the dispenser (10) and the first support (30) of the first container (20), wherein the step of holding comprises a holding of the first support (30) when in substantial correspondence of the second position (17) and/or at the end of the step of extraction (1001) and/or before the step of transportation (1004).

According to another non-limiting aspect, said step of transportation (1004) comprises a holding, through an auxiliary vacuum holder (19v), of at least a support (30) in correspondence of at least a respective collection head (19t) of the collector (19) through the creation of a vacuum between the at least a first support (30) and the collection head (19t), optionally wherein the holding of the at least a first support (30) takes place in correspondence of an its upper surface and/or wherein the step of transportation (1004) comprises a holding of the at least a first support (30) in correspondence of a lower end of the collection head (19t).

According to another non-limiting aspect, the holding of the at least a support (30) in correspondence of at least a respective collection head (19t) of the collector (19) through the creation of a vacuum between the at least a first support (30) and the collection head (19t) takes place alternatively to the holding of the at least a first support (30) in substantial correspondence of a holding hole (14) positioned on the dispenser (10) or on the auxiliary dispenser (10w).

According to another non-limiting aspect, said method comprises a step of measurement of a vacuum exerted by said vacuum holder and/or by said auxiliary vacuum holder (19v), in particular through at least a vacuum switch, and comprises a step of detection of a correct holding of the at least a support (30) through an electronic comparison of a signal, in particular of an electrical signal, transmitted by said vacuum switch with at least a threshold value of vacuum.

According to another non-limiting aspect, the method comprises a step of holding of the first support (30) of the second container (20) by means of the creation of a vacuum between said upper surface of the dispenser (10) and the first support (30) of the second container (20), wherein the step of holding comprises a holding of the first support (30) of the second container (20) when in substantial correspondence of the second position (17) and/or at the end of the step of extraction (1001) and/or before the step of transportation (1004).

According to another non-limiting aspect, the step of holding of the first support (30) of the second container (20) takes place simultaneously at the step of holding of the first support (30) of the first container (20) or takes place after the step of holding of the first support (30) of the first container (20) and after the step of controlled rotation (1007) or of relative movement between the extractor (18) and the dispenser (10).

According to another non-limiting aspect, the movement of the first support (30) takes place in a portion shaped and/or recessed (10r) of the upper surface, said first position (16) and said second position (17) being positioned in said portion shaped and/or recessed (10r).

According to another non-limiting aspect, the step of extraction (1001) comprises a rotation and/or translation of the extractor with respect to the dispenser (10).

According to another non-limiting aspect, the method comprises at least a second step of extraction (1001) of a first support (30) from a second container (20), by means of the extractor (18), and a step of relative movement between the extractor (18) and the dispenser (10) performed between said first step of extraction (1001) and said second step of extraction (1001) or comprises at least a second step of extraction (1001) of a second support (30) from the first container (20), by means of the extractor (18), and a relative movement between the extractor (18) and the dispenser (10).

According to another non-limiting aspect, said relative movement takes place after the second step of extraction (1001) and, optionally, does not take place between the first and the second step of extraction (1001).

According to another non-limiting aspect, the method further comprises a step of positioning of the dispenser (10) in an operating position in correspondence of which a first seat (11) of said plurality of seats (11) is in a predefined position of extraction configured and destined to allow the extraction of the at least a first support (30) from an upper end of the first container (20) housed in said first seat (11), by means of the extractor (18), and/or the movement (1002) of the at least a first support (30) takes place starting from an upper end of the first container (20) and an upper end of the first container (20) is in substantial correspondence of the first position (16).

According to another non-limiting aspect, said predefined position of extraction is configured and destined to allow the extraction of the at least a first support (30) from a supports unloading portion (20s) of the second container (20), in particular from a supports unloading end of the second container (20) directed upwards and facing itself substantially on the upper surface of the dispenser (10).

According to another non-limiting aspect, said predefined position of extraction is configured and destined to allow the extraction of the at least a first support (30) from a supports unloading portion (20s) of the second container (20), in particular from a supports unloading end of the second container (20) directed downwards and facing itself substantially on said upper surface of the dispenser (10).

According to another non-limiting aspect, the movement (1002) of the at least a first support (30) comprises a translation substantially through sliding, taking place between the first position (16) and the second position (17).

According to another non-limiting aspect, said sliding takes place at least partly on said dispenser (10), optionally along a direction of movement (Z) substantially axial.

According to another non-limiting aspect, the movement (1002) of the at least a first support (30) takes place by means of a thrust performed by an extraction finger (18s) performing in use a thrust of the at least a first support (30) in substantial sliding on the upper surface of the dispenser (10).

According to another non-limiting aspect, said direction of movement (Z) substantially axial is aligned between the first position (16) and the second position (17).

According to another non-limiting aspect, the step of transportation (1004) comprises a movement of the collector (19), said movement comprises at least one between a translation approaching and moving away with respect to the upper surface of the dispenser (10), in particular along an axis (W) of translation substantially vertical, and a translation approaching and moving away along a radial line, with respect to the dispenser (10) or substantially orthogonal with respect to the axis (W) of translation.

According to another non-limiting aspect, said movement is a composite movement.

According to another non-limiting aspect, the step of holding comprises a holding of the at least a first support (30) in substantial correspondence of a holding hole (14) operatively connected with said first vacuum holder (14v).

According to another non-limiting aspect, the holding hole (14) is in correspondence of the striking surface.

According to another non-limiting aspect, said holding hole (14) is in correspondence of the dispenser (10).

According to another non-limiting aspect, said holding hole (14) is in substantial correspondence of the upper surface of the dispenser (10).

According to another non-limiting aspect, the holding of the at least a first support (30) in said second extracted position (17) takes place on the dispenser (10).

According to another non-limiting aspect, said holding hole (14) is in correspondence of the auxiliary dispenser (10w).

According to another non-limiting aspect, said holding hole (14) is on the auxiliary dispenser (10w).

According to another non-limiting aspect, the holding hole (14) is in substantial correspondence of the upper surface of the auxiliary dispenser (10w).

According to another non-limiting aspect, said holding hole (14) is in substantial correspondence of an upper surface of the auxiliary dispenser (10w) and/or in substantial correspondence of the collection area of the auxiliary dispenser (10w).

According to another non-limiting aspect, the holding of the at least a first support (30) in said second extracted position (17) takes place on the auxiliary dispenser (10w).

According to another non-limiting aspect, the step of extraction (1001) comprises a movement (1002) of the at least a first support (30) on an auxiliary dispenser (10w) arranged in proximity of the dispenser (10) and configured for housing a plurality of supports (30), optionally in a plurality of collection areas (10r'), in particular in a respective plurality of collection areas (10r').

According to another non-limiting aspect, the second extracted position (17) is on said auxiliary dispenser (10w), in particular on an upper surface of the auxiliary dispenser (10w) and/or on a surface of the auxiliary dispenser accessible from above.

According to another non-limiting aspect, the method comprises a movement, in particular at least a rotation, of the auxiliary dispenser (10w), optionally said rotation taking place around a substantially vertical axis.

According to another non-limiting aspect, said rotation of the auxiliary dispenser (10w) takes place after the first step of extraction (1001).

According to another non-limiting aspect, the auxiliary dispenser (10w) comprises a plurality of collection areas (10r') destined, each one, to contain and/or retain at least a first support (30).

According to another non-limiting aspect, the movement, in particular the rotation, of the auxiliary dispenser (10w) determines a positioning of a predefined empty collection area (10r') in a position such that said second extracted position (17) corresponds substantially to said predefined empty collection area (10r'), optionally determining an alignment, in particular a substantially radial alignment, between a seat (11) and said empty collection area (10r').

According to another non-limiting aspect, the step of transportation (1004) comprises the transportation of a plurality of supports (30) from the auxiliary dispenser (10w) toward the culture plate (40).

According to another non-limiting aspect, the step of transportation (1004) comprises the simultaneous transportation of a plurality of supports (30) from a respective plurality of collection areas (10r') of the auxiliary dispenser (10w) toward the culture plate (40).

According to another non-limiting aspect, during the step of transportation (1004) the collector (19) performs an access to an upper surface of the auxiliary dispenser (10w) and performs a movement for transporting said plurality of supports (30) from the auxiliary dispenser (10w) toward the culture plate (40).

According to another non-limiting aspect, said movement is a composite movement.

According to another non-limiting aspect, said movement comprises at least one translation along a first and/or a second axis, and/or at least one rotation around a substantially vertical axis.

According to another non-limiting aspect, the first and the second axis are substantially inclined between them, optionally orthogonal.

According to another non-limiting aspect, the method comprises a controlled rotation of the dispenser (10) through a rotor.

According to another non-limiting aspect, the method comprises a step of transportation (1004) of the first support (30) from the second container (20) toward the culture plate (40).

According to another non-limiting aspect, the step of transportation (1004) of the first support (30) of the second container (20) toward the culture plate (40) by means of the collector (19) takes place when the rotor has rotated in controlled way the dispenser (10) and when it is performed at least the first step of extraction (1001).

According to the present disclosure is further described a method of distribution of supports (30) impregnated with antibiotics, comprising:
  a step (1000) of positioning of a plurality of tubular containers (20), each one containing a plurality of supports (30) impregnated with antibiotics and stacked, in a corresponding plurality of seats (11) of a dispenser (10),
  a first step of extraction (1001) of at least a first support (30) from a first container (20), by means of an extractor (18), the step of extraction (1001) being performed in correspondence of an end of the first container (20) and comprising a movement (1002) of the first support (30) between a first position (16) inside of the first container (20) and a second position (17) extracted from the first container wherein the first support (30) is positioned on an auxiliary dispenser (10w) different from the dispenser (10) and configured for housing a plurality of supports (30) in a respective plurality of collection areas (10r'),
  a step of collection of the first support (30) from the second position (17) by means of a collector (19),
  a step of transportation (1004) of the first support (30) from the auxiliary dispenser (10w) towards a culture plate (40) by means of the collector (19).

According to another non-limiting aspect, the step of extraction (1001) is performed in correspondence of an upper end of the first container (20) and/or the first position (16) inside of the first container (20) and/or the second position (17) extracted from the second container is in substantial correspondence of an upper surface of the dispenser (10) and/or of a same horizontal plane.

According to another non-limiting aspect, the method comprises a second step of extraction (1001) of at least a second support (30) from the first container (20), the second step of extraction (1001) being performed in correspondence of an end of the first container (20) and comprising a movement (1002) of the second support (30) between a first position (16) inside of the first container (20), and a second extracted position (17) wherein the second support (30) is positioned on the auxiliary dispenser (10w),
and/or comprises a second step of extraction (1001) of a first support (30) from a second container (20), by means of the extractor (18), the second step of extraction (1001) being performed in correspondence of an end of the second container (20) and comprising a movement (1002) of the first support (30) between a first position (16) inside of the second container (20), and a second extracted position (17) wherein the first support (30) is arranged on the auxiliary dispenser (10w).

According to another non-limiting aspect, the method comprises a step of collection, preferably simultaneous, of the first and of the second support (30) from the respective second positions (17) by means of the collector (19), and the step of transportation (1004) comprises the transportation, preferably simultaneous, of the first and/or of the second support (30) from the auxiliary dispenser (10w) toward the culture plate (40) by means of the collector (19).

According to another non-limiting aspect, the method comprises a step of relative movement, preferably performed through a rotation of the auxiliary dispenser (10w), between the auxiliary dispenser (10w) and the dispenser (10), for allowing the consecutive deposition on the auxiliary dispenser (10w) of said plurality of first supports (30) extracted from the corresponding plurality of containers (20) by means of the extractor (18).

According to another non-limiting aspect, the method comprises a step of rotation and/or translation (1009) of the auxiliary dispenser (10w) taking place after the first step of extraction (1001) and/or after the step of transportation (1004), in particular taking place after each step of extraction (1001) and/or after each step of transportation (1004).

According to another non-limiting aspect, said step of rotation or translation (1009) of the auxiliary dispenser (10w) determines a positioning of a collection area (10r') of the auxiliary dispenser (10w) in substantial alignment with said predefined position of extraction and/or with a direction of movement (Z) determined by the extractor (18).

According to another non-limiting aspect, said direction of movement (Z) is a direction of extraction.

According to another non-limiting aspect, during the step of transportation (1004) the collector (19) accesses to an upper surface of the auxiliary dispenser (10w) and performs a movement for transporting the plurality of supports (30) from the auxiliary dispenser (10w) toward the culture plate (40).

According to another non-limiting aspect, said movement is a composite movement and comprises at least one translation along a first and/or a second axis, and/or at least one rotation around a substantially vertical axis, optionally wherein the first and the second axis are substantially inclined between them, optionally orthogonal.

According to another non-limiting aspect, the method comprises a step of operation of a first vacuum holder (14v) and a holding of the first support (30) when in said second position (17) extracted through a vacuum exerted by the vacuum holder, wherein the holding of the first support (30) through the vacuum exerted by the first vacuum holder (14v) comprises a holding of the first support (30) in substantial correspondence of a holding hole (14) operatively connected with said first vacuum holder (14v) which is in correspondence of the auxiliary dispenser (10w).

According to another non-limiting aspect, the holding of the at least a first support (30) in said second extracted position (17) takes place on the auxiliary dispenser (10w).

According to another non-limiting aspect the method comprises a step of verification of a presence of the at least a first support (30) and/or a correct positioning of the at least a first support (30) on the culture plate (40) and/or on the auxiliary dispenser (10w), said step of verification being performed by means of an optical control system.

According to another non-limiting aspect, the step of verification is performed during and/or after the step of transportation (1004) of the first support (30) from the second position (17) toward the culture plate (40) and/or after the step of transportation (1004) from the auxiliary dispenser (10w) toward the culture plate (40) and/or during the step of extraction (1001) of the at least a first support (30).

According to another non-limiting aspect, the step of verification comprises an activation of at least one camera of the optical control system, and comprises a transmission of image data from the camera toward a data processing unit upon which is performed a software routine for the identification of a presence of the at least a first support (30) on the culture plate (40) and/or on the auxiliary dispenser (10w), and/or toward an electronic circuit of image processing, for the identification of a presence of the at least a first support (30) on the culture plate (40) and/or on the auxiliary dispenser (10w).

According to another non-limiting aspect, after said transmission of image data, the software routine causes the execution of an artificial intelligence algorithm, in particular implying the use of a neural network, destined to detect a presence and/or a shape and/or a size of said at least a first support (30).

According to another non-limiting aspect, the step (1000) of positioning of the plurality of containers (20) in the corresponding plurality of seats (11) of the dispenser (10) comprises a positioning of a first group of containers of said plurality of containers (20) in a first corresponding group of seats (11) of said plurality of seats (11), and comprises a positioning of a second group of containers of said plurality of containers (20) in a second corresponding group of seats (11) of said plurality of seats, wherein said first group of containers and said second group of containers differ by shape and/or by producer and/or wherein said first group of seats (11) differs in shape from said second group of seats (11).

According to another non-limiting aspect, the method comprises a step of reconfiguration of the dispenser (10) destined to cause an alteration of the shape of at least part of said plurality of seats (11) and/or of a number of said plurality of seats (11), optionally an alteration of the shape of said first group of seats (11) and/or of said second group of seats (11), and/or comprises a reconfiguration of a number and/or of a shape of at least part of the seats of the plurality of seats (11) of the dispenser (10).

According to another non-limiting aspect, the step of reconfiguration of the dispenser (10) and/or the reconfiguration of the number and/or of the shape of at least part of the seats of the plurality of seats (11) comprises a step of adaptation and/or replacement of at least one modular portion of said dispenser (10) positioned in substantial correspondence of at least part of the plurality of seats (11) and/or comprising at least one seat of said plurality of seats (11).

[Device]

According to the present disclosure it is also described a device (1) for distributing supports (30) impregnated with antibiotics, comprising:
- a dispenser (10), provided with a plurality of seats (11) configured for housing a corresponding plurality of tubular containers (20), each one containing a plurality of supports (30) impregnated with antibiotics and stacked, in such a way that respective upper ends of the tubular containers (20) result positioned substantially in correspondence of an upper surface of the dispenser (10);
- an extractor (18), configured for extracting (1001) at least a first support (30) from an upper end of a first tubular container (20) housed in a respective seat (11) of the dispenser (10), and for moving (1002) the first support (30) between a first position (16) inside the first container (20) and a second position (17) extracted from the first container (20), said first position (16) and said second position (17) lying substantially in correspondence of an upper surface of the dispenser (10) and/or of a same horizontal plane;
- a collector (19), configured for collecting the first support (30) from the second position (17) and for transporting (1004) the first support (30) from the second position (17) toward a culture plate (40).

According to the present disclosure it is also described a device (1) for distributing supports (30), comprising:
- a dispenser (10), provided with a plurality of seats (11) configured for housing a corresponding plurality of containers (20), each one containing a plurality of supports (30) stacked;
- an extractor (18), configured for extracting (1001) at least a first support (30) from a first tubular container (20) housed in a respective seat (11) of the dispenser (10), and for moving (1002) the first support (30) between a first position (16) inside the first container (20) and a second position (17) extracted from the first container (20);

a collector (19), configured for collecting the first support (30) from the second position (17) and for transporting (1004) the first support (30) from the second position (17) towards a culture plate (40).

According to another non-limiting aspect, the plurality of containers (20) is a plurality of tubular containers (20).

According to another non-limiting aspect, the plurality of seats (11) is configured in such a way that respective upper ends of the tubular containers (20) result positioned substantially in correspondence of an upper surface of the dispenser (10).

According to another non-limiting aspect, the plurality of seats (11) is configured in such a way that respective lower ends of the tubular containers (20) result positioned substantially in correspondence of a surface of the dispenser (10) accessible from above.

According to another non-limiting aspect, the extractor (18) is positioned in substantial correspondence of the, and/or is operatively associated to, dispenser (10).

According to another non-limiting aspect, the extractor (18) is configured for extracting (1001) at least a first support (30) from an upper end of the first tubular container (20) housed in a respective seat (11) of the dispenser (10).

According to another non-limiting aspect, the extractor (18) is configured for extracting (1001) at least a first support (30) from a lower end of the first tubular container (20) housed in a respective seat (11) of the dispenser.

According to another non-limiting aspect, said first position (16) and said second position (17) lie substantially in correspondence of an upper surface of the dispenser (10) and/or of a same horizontal plane.

According to another non-limiting aspect, the extractor (18) is configured for performing a movement of rotation and/or translation with respect to the dispenser (10) and/or is configured for extracting (1001) at least a first support (30) through a movement of rotation and/or di translation.

According to another non-limiting aspect, the device (1) comprises a supporting frame (100) upon which the dispenser (10) is movably mounted, preferrably rotatably and/or translatably mounted, in such a way that the dispenser (10) results movable relatively to the extractor (18) for selectively and sequentially positioning the tubular containers (20), in individual or grouped way, in correspondence of the extractor (18) for allowing the extraction of the first supports from the tubular containers; or further comprising a supporting frame (100) upon which the extractor (18) is movably mounted, preferably rotatably and/or translatably mounted, in such a way that the extractor (18) results movable relatively to the dispenser (10) for selectively and sequentially positioning itself in correspondence of one or more of the tubular containers (20), for allowing the extraction of the first supports from the tubular containers (20).

According to another non-limiting aspect, the collector (19) is configured for depositing the at least a first support (30) on the culture plate (40).

According to another non-limiting aspect, the extractor (18) is configured for extracting (1001) at least a first support (30) from an upper end of a second tubular container (20) housed in a respective seat (11) of the dispenser (10), and for moving (1002) the first support (30) between a first position (16) inside the second container (20) and a second position (17) extracted from the second container (20).

According to another non-limiting aspect, the device (1) is configured for performing a step of relative movement between the extractor (18) and the dispenser (10), performed between the extraction of the first support (30) of the first container (20) and the extraction of the first support (30) of the second container (20).

According to another non-limiting aspect, the extractor (18) is configured for performing a plurality of steps of extraction (1001) of a plurality of first supports (30) from a plurality of tubular containers (20) housed in the respective seats (11) and for moving said first supports (30) between the first position (16) and the second position (17) or between respective first positions (16) and respective second positions (17), optionally lying substantially in correspondence of an upper surface of the dispenser (10).

According to another non-limiting aspect, the device (1) is configured for performing a plurality of steps of relative movement between the extractor (18) and the dispenser (10), performed each one between two of said steps of extraction (1001).

According to another non-limiting aspect, the extractor (18) is configured for performing a rotation and/or translation with respect to the dispenser (10) and/or the dispenser (10) is configured for performing a rotation and/or a translation with respect to the extractor (18).

According to another non-limiting aspect, the device (1) is configured for causing the rotation and/or the translation of the dispenser (10) between two steps of extraction and/or after the transportation (1004) of the first support (30) from the second position (17) toward the culture plate (40).

According to another non-limiting aspect, the device is configured for positioning the dispenser (10) in an operating position in correspondence of which a first seat (11) of said plurality of seats (11) is in a predefined position of extraction configured and destined to allow the extraction of the at least a first support (30) from an upper end of the first container (20) housed in said first seat (11), by means of the extractor (18), and/or the extractor (18) is configured for moving (1002) the first support (30) between the first position (16) and the second position (17) starting from an upper end of the first container (20).

According to another non-limiting aspect, the upper end of the first container (20) is in substantial correspondence of the first position (16), optionally the extractor (18) being configured for extracting (1001) the at least a first support (30) from a supports unloading portion (20s) of the first container (20), in particular from an end of supports (30) unloading of the first container (20) directed upwards and substantially facing on said upper surface of the dispenser (10).

According to another non-limiting aspect, the device comprises a rotor, optionally automatically controlled, configured for causing a controlled rotation (1007) of the dispenser (10) so that a second seat (11) of said plurality of seats (11) of the dispenser (10) is in said predefined position of extraction configured and destined to allow the extraction of the at least a first support (30) from an upper end of a second container (20) housed in said second seat (11), by means of the extractor (18).

According to another non-limiting aspect, the dispenser (10) has an at least partially circular configuration and the seats (11) are arranged according to a substantially circular arrangement in the dispenser (10), which is configured for rotating during the steps of movement of the dispenser (10) between the extraction positions.

According to another non-limiting aspect, the extractor (18) is configured for moving (1002) the first support (30) between the first position (16) and the second position (17) through a translation along a direction substantially radial with respect to a centre of the dispenser (10), optionally through a translation along a direction radially external with respect to the centre of the dispenser (10) or through a translation along a direction radially internal with respect to the centre of the dispenser (10).

According to another non-limiting aspect, the device (1) comprises at least a first vacuum holder (14v) configured for creating a vacuum between a striking surface and the first support (30), wherein the first vacuum holder (14v) is configured for holding the at least a first support (30) in substantial correspondence of the second position (17) and/or of the collector (19).

According to another non-limiting aspect, the device (1) comprises at least a first vacuum holder (14v) configured for creating a vacuum between a striking surface and the first support (30), wherein the first vacuum holder (14v) is configured for holding the at least a first support (30) after the movement performed by the extractor (18) and/or before the transportation (1004) performed by said collector (19) and/or during the collection and/or the transportation (1004).

According to another non-limiting aspect, the device (1) comprises at least a first vacuum holder (14v) configured for creating a vacuum between said upper surface of the dispenser (10) and the first support (30) of the first container (20), wherein the first vacuum holder (14v) is configured for holding the first support (30) of the first container (20) when in substantial correspondence of the second position (17) and/or after the movement performed by the extractor (18) and/or before the transportation performed by said collector (19).

According to another non-limiting aspect, said striking surface is at least one between an upper surface of the dispenser (10), or a surface of the dispenser (10) accessible from above, or is a surface in substantial correspondence of a collection area of an auxiliary dispenser (10w) configured for housing a plurality of supports (30) in a respective plurality of collection areas (10r').

According to another non-limiting aspect, the collector (19) comprises at least one collection head (19t), operatively connected with, or comprising, an auxiliary vacuum holder (19v) and configured for holding at least a respective first support (30) through the creation of a vacuum between the at least a first support (30) and the collection head (19t), optionally said collection head (19t) being configured for holding the at least a first support (30) in correspondence of an upper surface of the first support (30) and/or said collector (19) being configured for holding the at least a first support (30) in correspondence of a lower end portion of the collection head (19t).

According to another non-limiting aspect, the device (1) is configured for causing the holding of the at least a support (30) in correspondence of at least one respective collection head (19t) of the collector (19) through the creation of a vacuum between the at least a first support (30) and the collection head (19t) alternatively to the holding of the at least a first support (30) in substantial correspondence of a holding hole (14) positioned on the dispenser (10) or on the auxiliary dispenser (10w).

According to another non-limiting aspect, the device (1) comprises at least a vacuum switch configured for performing a measurement of a vacuum exerted by said vacuum holder and/or by said auxiliary vacuum holder (19v); said device (1) being configured for performing an electronic comparison between a signal, in particular an electric signal, transmitted in use by said vacuum switch with at least a vacuum threshold value, said comparison being destined to detect a correct holding of the at least a support (30) through an electronic comparison of a signal, in particular of an electric signal, transmitted by said vacuum switch with at least a vacuum threshold value.

According to another non-limiting aspect, the device (1) comprises at least a second vacuum holder (14v') configured for creating a vacuum between said upper surface of the dispenser (10) and the first support (30) of the second container (20).

According to another non-limiting aspect, the second vacuum holder (14v') is configured for holding the first support (30) of the second container (20) when in substantial correspondence of the second position (17) and/or after the movement performed by the extractor (18) and/or before the transportation performed by said collector (19).

According to another non-limiting aspect, the device (1) is configured for activating the first vacuum holder (14v) simultaneously with the second vacuum holder (14v'), or for activating the second vacuum holder (14v') after the activation of the first vacuum holder (14v) and after the activation of the rotor.

According to another non-limiting aspect, the upper surface comprises a portion shaped and/or recessed (10r) and said first position (16) and said second position (17) are in said portion shaped and/or recessed (10r) and/or the extractor (18) is configured for moving the support (30) within said portion shaped and/or recessed (10r).

According to another non-limiting aspect, the extractor (18) is configured for extracting, in particular in a second step of extraction (1001), at least a first support (30) from a second container (20), and for moving (1002) the first support (30) between the first position (16) and the second position (17).

According to another non-limiting aspect, the device (1) is configured for performing a step of relative movement between the extractor (18) and the dispenser (10), performed between the first step of extraction (1001) and the second step of extraction (1001), or
the extractor (18) is configured for performing an extraction (1001) of at least a second support (30) from the first container (20) and for moving the second support (30) between the first position (16) and the second position (17).

According to another non-limiting aspect, the device (1) is configured for performing a step of relative movement between the extractor (18) and the dispenser (10), performed after the second step of extraction (1001), optionally not between the first and the second step of extraction.

According to another non-limiting aspect, the extractor (18) is configured for performing a rotation and/or translation with respect to the dispenser (10) and/or the dispenser (10) is configured for performing a rotation and/or a translation.

According to another non-limiting aspect, the device (1) is configured for causing the rotation and/or the translation of the dispenser (10) at least in correspondence of the first step of extraction (1001) and/or after the first step of extraction (1001) and/or after the transportation (1004) of the first support (30) from the second position (17) toward the culture plate (40).

According to another non-limiting aspect, the device (1) is configured for positioning the dispenser (10) in an operating position in correspondence of which a first seat (11) of said plurality of seats (11) is in a predefined position of extraction configured and destined to allow the extraction of the at least a first support (30) from an upper end of the first container (20) housed in said first seat (11), by means of the extractor (18), and/or the extractor (18) is configured for moving (1002) the first support (30) between the first position (16) and the second position (17) starting from an upper end of the first container (20).

According to another non-limiting aspect, the upper end of the first container (20) is in substantial correspondence of the first position (16), optionally the extractor (18) being configured for extracting (1001) the at least a first support (30) from a supports unloading portion (20s) of the first container (20), in particular from a supports unloading end (30) of the first container (20) directed upwards and substantially facing on said upper surface of the dispenser (10).

According to another non-limiting aspect, the extractor (18) is configured for moving the at least a first support (30) in substantial sliding on the upper surface of the dispenser (10), optionally along a direction of movement (Z) substantially axial.

According to another non-limiting aspect, the extractor (18) comprises an extraction finger (18s) configured for pushing at least the first support (30) in substantial sliding on the upper surface of the dispenser (10), optionally along a substantially axial direction of movement (Z).

According to another non-limiting aspect, said substantially axial direction of movement (Z) is aligned between the first position (16) and the second position (17).

According to another non-limiting aspect, the collector (19) is configured for performing a movement comprising at least one between a translation approaching and moving away with respect to the upper surface of the dispenser (10) or with respect to the surface of the dispenser (10) accessible from above, in particular along an axis (W) of translation substantially vertical, and/or a translation approaching and moving away along a direction substantially radial with respect to the dispenser (10) or substantially orthogonal with respect to the axis (W) of translation.

According to another non-limiting aspect, said movement is a composite movement.

According to another non-limiting aspect, the device (1) comprises at least one holding hole (14) operatively connected with the first vacuum holder (14v), and is configured for holding the at least a first support (30) in substantial correspondence of the at least one holding hole (14).

According to another non-limiting aspect, the holding hole (14) is positioned on said striking surface.

According to another non-limiting aspect, said at least one holding hole (14) is in correspondence of the dispenser (10).

According to another non-limiting aspect, said at least one holding hole (14) is in correspondence of the auxiliary dispenser (10w).

According to another non-limiting aspect, the holding of the at least a first support (30) in said second extracted position (17) takes place on the auxiliary dispenser (10w).

According to another non-limiting aspect, the device (1) comprises an auxiliary dispenser (10w) configured for housing a plurality of supports (30), optionally in a plurality of collection areas (10r'), in particular in a respective plurality of collection areas (10r').

According to another non-limiting aspect, the device (1) is configured for performing a movement (1002) of the at least a first support (30) on the auxiliary dispenser (10w), optionally on an upper surface of the auxiliary dispenser (10w).

According to another non-limiting aspect, the second extracted position (17) is on said auxiliary dispenser (10w), in particular on an upper surface of the auxiliary dispenser (10w) and/or on a surface of the auxiliary dispenser (10w) accessible from above.

According to another non-limiting aspect, the device (1) is configured for causing a movement, in particular at least one rotation, of the auxiliary dispenser (10w), optionally said rotation taking place around a substantially vertical axis.

According to another non-limiting aspect, the auxiliary dispenser (10w) comprises a plurality of collection areas (10r') designed, each one, to contain and/or retain at least a first support (30).

According to another non-limiting aspect, the movement, in particular the rotation, of the auxiliary dispenser (10w) determines a positioning of a predefined empty collection area (10r') in a position such that said second extracted position (17) corresponds substantially to said predefined empty collection area (10r'), optionally determining an alignment, in particular a substantially radial alignment, between a seat (11) and said empty collection area (10r').

According to another non-limiting aspect, the collector (19) is configured for transporting a plurality of supports (30) from the auxiliary dispenser (10w) toward the culture plate (40).

According to another non-limiting aspect, the collector (19) is configured for transporting simultaneously a plurality of supports (30) from a respective plurality of collection areas (10r) of the auxiliary dispenser (10w) toward the culture plate (40).

According to another non-limiting aspect, the collector (19) is configured for performing a composite movement for transporting said plurality of supports (30) from the auxiliary dispenser (10w) toward the culture plate (40).

According to another non-limiting aspect, said composite movement comprises at least one translation along a first and/or a second axis, and/or comprises at least one rotation around an axis substantially vertical.

According to another non-limiting aspect, the first and the second axis are substantially inclined between them, optionally orthogonal.

According to another non-limiting aspect, said first position (16) is a position accessible from a lateral and/or lower portion or wall of the dispenser (10).

According to another non-limiting aspect, the support (30) is impregnated with a substantially fluid or liquid substance, optionally comprising a medicinal, optionally an antibiotic.

According to another non-limiting aspect, the support (30) has substantially discoidal shape.

According to another non-limiting aspect, the seat (11) is a substantially axial hole and comprises a main development axis.

According to another non-limiting aspect, the main development axis of the seat (11) is substantially parallel to a rotation axis of the dispenser (10) and/or to a relative rotation axis between the dispenser (10) and the collector (19) and/or is substantially vertical.

According to another non-limiting aspect, the seat (11) comprises a slotted portion (11a) axially extending for at least part of the, optionally substantially for the whole, extension of the seat (11) along said main development axis.

According to another non-limiting aspect, the collector (19) is configured for collecting the support (30) through the execution of a vacuum exerted on a surface of the support (30).

According to another non-limiting aspect, said first position (16) and said second position (17) are accessible from a substantially inclined direction with respect to a direction of support extraction (30) and face on the outside of the dispenser (10).

According to another non-limiting aspect, the substantially inclined direction with respect to a direction of support extraction (30) is a substantially vertical direction.

According to another non-limiting aspect, the device (1) comprises a rotor configured for rotating the dispenser (10) in controlled way.

According to another non-limiting aspect, the collector (19) is configured for collecting the at least a first support (30) extracted from the second container (20) when the rotor has rotated in controlled way the dispenser (10) and when the extractor (18) has performed the first step of extraction (1001).

According to another non-limiting aspect, the plurality of seats (11) is configured for allowing the introduction of a respective container (20) in a position such that a supports unloading portion (20s) of the first container (20), in particular a discs unloading end of the first container (20), is directed upwards and faces substantially on said upper surface of the rotatable dispenser (10).

According to another non-limiting aspect, the plurality of seats (11) is configured for allowing the introduction of a respective container (20) in a position such that a supports unloading portion (20s) of the first container (20), in particular a discs unloading end of the first container (20), is directed downwards and faces substantially on said upper surface of the rotatable dispenser (10).

According to the present disclosure, it is also described a device (1) for distributing of supports (30) impregnated with antibiotics, comprising:
- a dispenser (10), provided with a plurality of seats (11) configured for housing a corresponding plurality of tubular containers (20), each one containing a plurality of supports (30) impregnated with antibiotics and stacked,
- an auxiliary dispenser (10w) configured for housing a plurality of supports (30) in a respective plurality of collection areas (10r'),
- an extractor (18), configured for extracting (1001) at least a first support (30) from an end of a first tubular container (20) housed in a respective seat (11) of the dispenser (10), and for moving (1002) the first support (30) between a first position (16) inside the first container (20) and a second position (17) extracted from first container (20) wherein the at least a first support (30) is arranged on the auxiliary dispenser (10w),
- a collector (19), configured for collecting the first support (30) from the second position (17) and for transporting (1004) the first support (30) from the auxiliary dispenser (10w) towards a culture plate (40).

According to another non-limiting aspect, the device further comprises a supporting frame (100) upon which the dispenser (10) is movably mounted, preferably rotatably and/or translatably mounted, in such a way that the dispenser (10) results movable relatively to the extractor (18) for selectively and sequentially positioning the tubular containers (20), in individual or grouped way, in correspondence of the extractor (18) for allowing the extraction of the first supports from the tubular containers; or comprises also a supporting frame (100) upon which the extractor (18) is movably mounted, preferably rotatably and/or translatably mounted, in such a way that the extractor (18) results movable relatively to the dispenser (10) for selectively and sequentially positioning itself in correspondence of one or more of the tubular containers (20), for allowing the extraction of the first supports from the tubular containers and/or comprises also a supporting frame (100) upon which the auxiliary dispenser (10w) is movably mounted, preferably rotatably and/or translatably mounted, for allowing the consecutive deposition on the auxiliary dispenser (10w) of said plurality of first supports (30) extracted from the corresponding plurality of containers (20) by means of the extractor (18).

According to another non-limiting aspect, the extractor (18) is positioned and configured for extracting the first support in correspondence of an upper end of the first container (20) housed in the respective seat of the dispenser, and/or the first position (16) inside the first container (20) and/or the second position (17) extracted from the second container are in substantial correspondence of an upper surface of the dispenser (10) and/or of a same horizontal plane.

According to another non-limiting aspect, the extractor (18) is configured for extracting at least a second support (30) from the first container (20), and for moving (1002) the second support (30) between the first position (16) inside the first container (20) and the second extracted position (17) wherein the second support (30) is arranged on the auxiliary dispenser (10w),
and/or the extractor (18) is configured for extracting at least a first support (30) from a second container (20), and for moving (1002) the first support (30) between the first position (16) inside the second container (20) and the second extracted position (17) wherein the first support (30) is positioned on the auxiliary dispenser (10w).

According to another non-limiting aspect, the collector (19) is configured for collecting, preferably simultaneously, the first and the second support (30) from the respective second positions (17) and for transporting (1004) preferably simultaneously, the first and the second support (30) from the auxiliary dispenser (10w) towards a culture plate (40).

According to another non-limiting aspect, the dispenser (10) is configured for performing a rotation and/or a translation; the device (1) being configured for causing the rotation and/or the translation of the dispenser (10) after the first step of extraction (1001), in particular when both the first and the second step of extraction (1001) took place and/or between two steps of extraction and/or after the transportation (1004) of the first support (30) from the auxiliary dispenser (10w) toward the culture plate (40).

According to another non-limiting aspect, the device (1) comprises a mover, optionally automatically controlled, configured for causing a controlled rotation and/or a translation (1009) of the auxiliary dispenser (10w) after the first step of extraction (1001) and/or when the collector (19) has transported (1004) the first support (30) from the auxiliary dispenser (10w) toward the culture plate (40), wherein optionally the device (1) is configured for causing a rotation (1009) of the auxiliary dispenser (10w) after each step of extraction (1001) and/or after each transportation (1004) of a support (30) toward the culture plate (40).

According to another non-limiting aspect, said rotation or translation (1009) of the auxiliary dispenser (10w) determines a positioning of a collection area (10r') of said auxiliary dispenser (10w) in substantial alignment with said predefined position of extraction and/or with a direction of movement (Z) determined by the extractor (18).

According to another non-limiting aspect, the collector (19) is configured for accessing, during the transportation (1004), an upper surface of the auxiliary dispenser (10w) and performs a movement for transporting said plurality of supports (30) from the auxiliary dispenser (10w) toward the culture plate (40), said movement being a composite movement and comprising at least one translation along a first and/or a second axis and/or at least one rotation around a substantially vertical axis, optionally wherein the first and the second axis are substantially inclined between them, optionally orthogonal.

According to another non-limiting aspect, the upper surface of the auxiliary dispenser (10w) comprises at least one portion shaped and/or recessed, said portion shaped and/or recessed being in substantial correspondence of a collection area and/or of a plurality of collection areas.

According to another non-limiting aspect, the device (1) comprises an optical control system, configured for, and destined to, verify a presence of the at least a first support (30) and/or a correct positioning of the at least a first support (30) on the culture plate (40) and/or on the auxiliary dispenser (10w).

According to another non-limiting aspect, the optical control system is configured and specifically adapted to be activated during and/or after the step of transportation (1004) of the first support (30) from the second position (17) toward the culture plate (40) and/or after the step of transportation (1004) from the auxiliary dispenser (10w) toward the culture plate (40) and/or during the extraction (1001) of the at least a first support (30).

According to another non-limiting aspect, the optical control system comprises at least one camera, operatively connected with a data processing unit upon which is performed a software routine for the identification of a presence of the at least a first support (30) on the culture plate (40) and/or on the auxiliary dispenser (10w), and/or operatively connected with an image processing electronic circuit, for the identification of a presence of the at least a first support (30) on the culture plate (40) and/or on the auxiliary dispenser (10w).

According to another non-limiting aspect, the software routine causes the execution of an artificial intelligence algorithm, in particular implying the use of a neural network, destined to detect a presence and/or a shape and/or a size of said at least a first support (30).

According to another non-limiting aspect, the plurality of seats (11) comprises a first group of seats (11) configured or reconfigurable for housing a corresponding first group of containers (20) of said plurality of containers (20), and a second group of seats (11) configured or reconfigurable for housing a corresponding second group of containers (20) of said plurality of containers (20), wherein said first group of containers (20) and said second group of containers differ by shape and/or by producer and/or wherein said first group of seats (11) differs in shape from said second group of seats (11).

According to another non-limiting aspect, the dispenser (10) is a dispenser reconfigurable for determining an alteration of the shape of at least part of the plurality of seats (11) and/or for determining an alteration of the number of the plurality of seats (11), optionally the dispenser (10) being reconfigurable for determining an alteration of the shape of the first group of seats (11) and/or of the second group of seats (11).

According to another non-limiting aspect, the dispenser (10) is a modular dispenser, and comprises at least one modular portion adaptable and/or replaceable for determining said alteration of the shape of at least part of the plurality of seats (11) and/or of the number of said plurality of seats (11), said modular portion being positioned in substantial correspondence of at least part of the plurality of seats (11) and/or comprising at least one of said plurality of seats (11).

According to another non-limiting aspect, the modular portion is designed e specifically configured for determining a reconfiguration of at least one seat of the plurality of seats.

[Computer Program]

According to another aspect, it is described a computer program, stored on a non-transitory memory support, wherein the computer program is suitable for being performed by at least a data processing unit, the computer program comprising portions of software code that when performed cause the execution of the steps of the method according to one or more of the aspects here described, optionally with the exclusion of the step (1000) of positioning.

[Kit]

According to the present disclosure it is described a kit comprising a device (1) according to one or more of the aspects here described, and at least a container (20).

According to another non-limiting aspect, the container (20) comprises a body that defines a cavity (22) configured per housing a plurality of supports (30).

According to another non-limiting aspect, the body develops along a substantially axial direction and/or the cavity (22) develops along a substantially axial direction.

According to another non-limiting aspect, the container (20) comprises at least one pusher configured for exerting a force on the plurality of supports (30); optionally said pusher being installed inside said cavity (22).

According to another non-limiting aspect, the container (20) comprises at least one spring (21) installed between a striking portion (24) of said body and said pusher; said spring lying in a compressed configuration so that to cause said force on the plurality of supports (30).

According to another non-limiting aspect, the container (20) comprises at least one supports unloading portion (20s) comprising at least a retainer (23) partially obstructing the cavity (22); the retainer (23) comprising optionally an angled portion and arranged such that to stop at least a support (30) in a position of extraction wherein said support (30) exits at least partially from the body, in particular from the cavity, of the container (20) and in such a way as to allow an extraction through sliding and/or pushing and/or pulling along a substantially oblique direction, in particular orthogonal, with respect to a pushing direction of a device pusher, optionally of the extractor (18).

[Use]

According to the present disclosure it is described the use of the device (1) according to one or more of the aspects here described for the execution of antibiotics susceptibility tests (AST).

BRIEF DESCRIPTION OF THE DRAWINGS

The present disclosure continues with a detailed description of some of the preferred embodiments of the device and of the method. This detailed description refers to the attached figures, a description thereof is herein provided.

DETAILED DESCRIPTION

Figure 1:
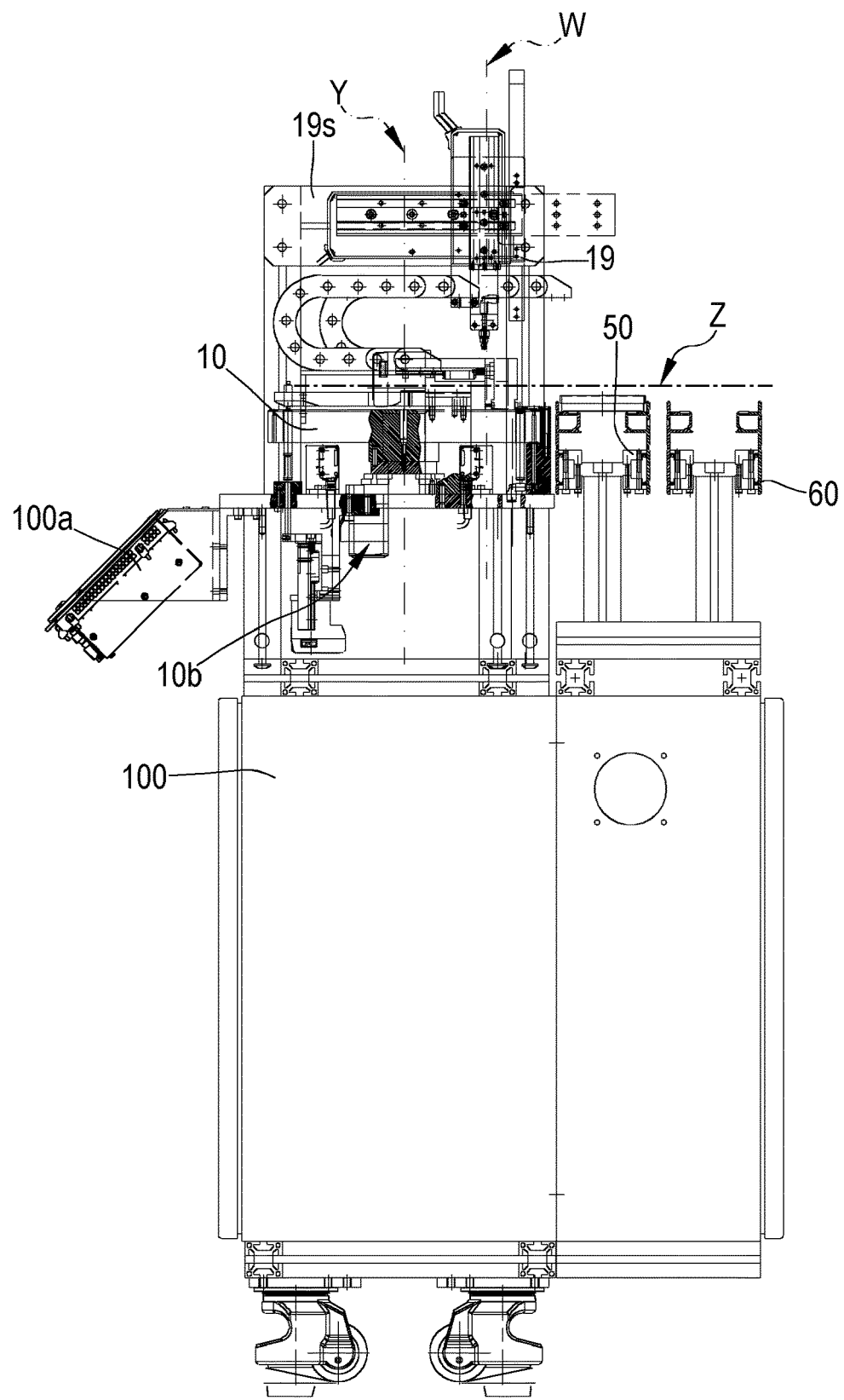
FIG. 1 shows a lateral schematic representation of a device for the distribution of impregnable or impregnated supports according to the present disclosure.

In FIG. 1 the reference number 1 identifies as a whole a device for the distribution of impregnable or impregnated supports. This device realizes a system for distributing impregnable or impregnated supports in order to allow to realize antibiotic susceptibility tests (AST).

The device 1 first of all comprises a supporting frame 100 upon which is positioned a dispenser 10 for containers 20 in use containing a plurality of supports 30 impregnable or impregnated with a substantially fluid or liquid substance, optionally comprising a medicament, more particularly and preferably an antibiotic. The dispenser 10 is provided with at least a plurality of seats 11, each of which is configured for housing at least a first container 20. In particular, each of the seats 11 comprises a hole, which preferably, as it can be seen in at least part of the attached figures, has a substantially vertical axis.

In a preferred but non-limiting embodiment, the number of seats 11 housed in the dispenser 10 is equal to 50; this allows to have a large number of containers 20 pre-loaded on the dispenser 10 and allows to keep an automated functioning of the device 1 without the need for further loading of containers 20 for a sufficiently long time. Having a relatively large number of seats 11 in the dispenser 10 allows to make an overall faster functioning of the device 1.

The dispenser 10 may be configured such that the shape and/or size of the seats 11 may be quickly varied. In a preferred embodiment, the dispenser 10 is realized through a plurality of modular elements that allow to adapt the shape and/or size of the seats 11 according to the requirements, thereby allowing an adaptation to containers 20 whose characteristics may be variable according to the specific manufacturer.

Although in the attached figures the seats 11 all have a same size, this should not be understood as limiting. In fact, some embodiments of the device 1, conceived by the Applicant but not represented in detail in the figures attached to the present description, could be provided with seats 11 having different sizes and/or shapes, thus able to house containers 20 of different type.

In particular, in an embodiment, the dispenser 10 is adapted by appropriately configuring at least some of the modular elements or replacing at least some of them, such that the plurality of containers 20 housed comprises a first group of containers 20 of a first type and/or manufacturer and/or shape, and a second group of containers 20 of a second type and/or manufacturer and/or shape. For the purposes of the present disclosure, "shape" of the container 20 means any shape among a shape of a cross-sectional shape of the container 20, in particular a diameter, a length, a width, a depth, a construction material. The modular elements are positioned in a radially outer position of the dispenser 10, but this should not be understood in a limiting manner.

In an embodiment, a modular element comprises at least one seat 11; alternatively, in a further embodiment, a modular element comprises a part of a seat, the remaining part of the seat being formed on a fixed portion of the dispenser 10, not designed to be replaced in use.

Thanks to this technical feature, the use of the dispenser 10 becomes particularly flexible; in fact, it may happen that momentary shortages of supply of containers 20 of a first shape, may lead to the impossibility of completely loading the dispenser 10. Through the configuration of part of the modular elements or the at least partial replacement of themselves, it is possible to provide for a complete loading of the dispenser 10 with heterogeneous containers 20, without affecting the functionality and/or operating performance of the device 1. The replacement or introduction of one or more modular elements also allows a variation of an overall number of seats 11 available on the dispenser 10.

As it will become clear prosecuting the reading of the description, the advantages deriving from the adaptability to containers 20 of different type are particularly important in a device 1 in which the movement of the supports extracted from the containers takes place on a surface of the dispenser 10 that is an upper surface or in any case accessible from above, since in such a case the flexibility deriving from the possibility of extracting supports from containers 20 of different type is maximized by the absence of constraints and/or mechanical parts that is obtained by working on an upper, or accessible from above, surface substantially free.

In an embodiment, the dispenser 10 is in a substantially discoidal shape and detects an upper surface, a lower surface opposite with respect to the upper surface, and a lateral surface interposed between the upper surface and the lower surface. In a non-limiting embodiment, the lateral surface extends along a direction substantially orthogonal with respect to the planes on which the upper surface and the lower surface lie.

FIG. 1 also shows a collector 19 of a movable type, and installed in a supporting castle 19s, which in turn is supported by the supporting frame 100 of the device 1. Such a collector 19 is configured for collecting at least one support 30 from the dispenser 10 and for transporting the support 30 from the dispenser 10 to a culture plate 40. Although this feature should not be understood in a limiting manner, the supporting frame 100 may be realized in aluminium, so as to be both robust and light.

A first and second conveyor belt 50, 60, for example of a rubberized type, are also shown in the non-limiting embodiment of the device 1 in FIG. 1. Said first and second conveyor belt 50, 60 are configured for supporting the culture plate 40 and for moving the same at least from an arrival position to a deposit position in which the culture plate 40 is in a position suitable for the deposit of the support 30 transported by the collector 19, and between said deposit position to a destination position in which the culture plate 40 with at least one support 30 is directed for further processing, in particular (but not limited to) for performing the antibiotic susceptibility test. The control of the movement of the first and second conveyor belt 50, 60 is performed by the data processing unit, which sends movement signals to servo actuators, in particular electric motors operatively connected each one to the respective first and second conveyor belt 50, 60. The electric motors may for example be stepper type.

The aforementioned elements are supported by the supporting frame 100, which in an embodiment comprises lateral walls suitable for covering an internal componentry of the device 1 necessary to allow the movement of the various elements thereof described herein, including a data processing unit.

A user interface 100u is provided at an appropriate height to allow the control of the device 1 by an operator. The user interface 100u is operatively connected to the data processing unit, preferably but not limited thereto through a wired connection. The supporting frame is also intended to make the user interface 100u lie at a height convenient for use by an operator of normal height.

Guided user interfaces (GUIs) may be executed on the user interface to allow the operator to control of the functioning of the device 1, in particular a step of loading at least one container 20 on the dispenser 10, in an easy manner, preventing the occurrence of errors. In a non-limiting embodiment, the GUI may guide the operator in scanning an identification code present on the container 20 so that the data processing unit is able to associate determined characteristics of the supports 30 present in the container 20 with the container 20 itself, to perform calibrations and/or configuration adaptations of the device 1 in a substantially automated manner and in association with the specific nature of the supports 30 and/or of the container 20.

Figure 2:
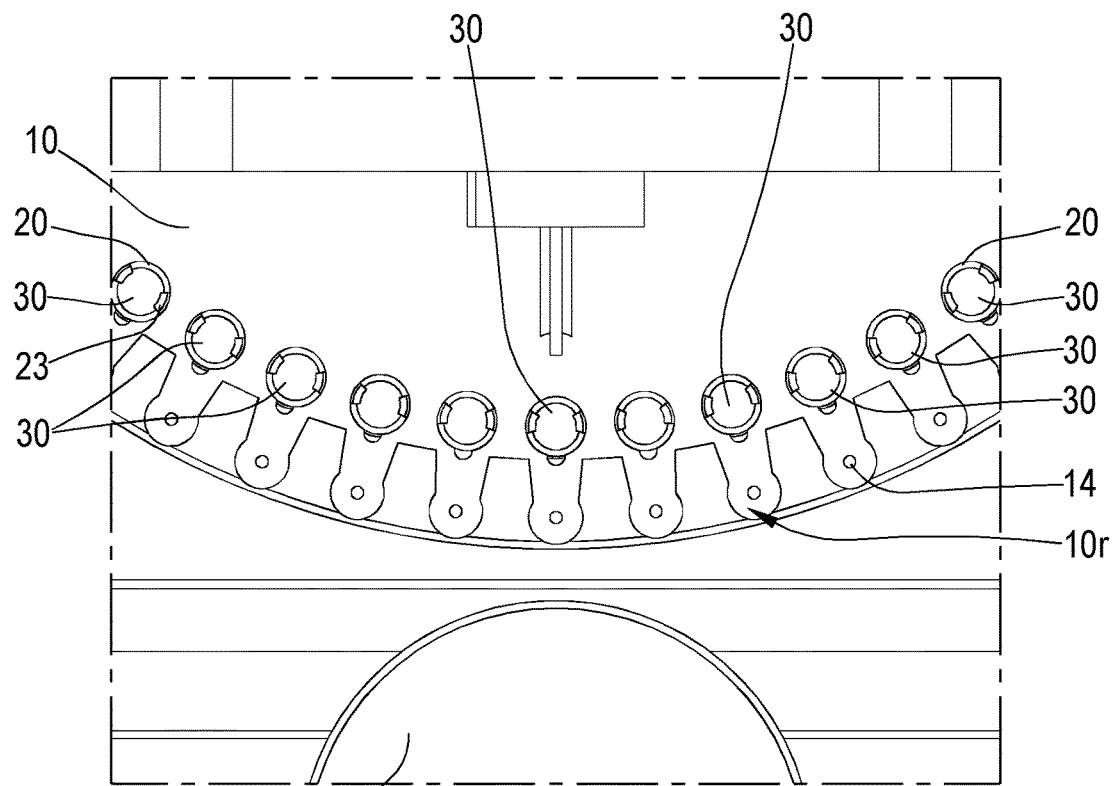
FIG. 2 shows a plan view of a portion of the device object of the present disclosure.

As it can be seen from FIG. 2, in a non-limiting embodiment, the dispenser 10 comprises a plurality of seats 11 arranged in a substantially outer perimeter position and opening on the upper surface. Such seats are preferably aligned along a substantially inclined direction with respect to the plane on which the upper surface of the dispenser 10 lies; in the embodiment shown in the figures, the seats 11 extend axially along a substantially vertical main development axis and orthogonal with respect to the upper surface of the dispenser 10. Preferably, each seat 11 comprises a slotted portion 11a axially extending for at least part of, optionally substantially all of, the extension of the seat 11 along the main development axis.

Although in a perimeter outer position, the seats 11 are aligned on an ideal internal circumference with respect to an outer circumference along which are aligned upper surface portions intended to temporarily retain each at least one respective support 30 extracted from the container 20 in the modes to be described below. For this reason, and for the purposes of the present disclosure, the seats 11 are in substantially correspondence of a first radially internal position 16 of the dispenser 10 and the upper surface portions intended to temporarily hold each at least one respective support 30 are in a second radially outer position 17 of the dispenser 10.

The upper surface of the dispenser 10 comprises a plurality of shaped and/or recessed portions 10r with respect to a portion 13 of the upper surface lying at a higher height. In correspondence with each of the shaped and/or recessed portions there are the seat 11 and the portion of the upper surface intended to temporarily retain at least one respective support 30 extracted from the container 20. For this reason, it can be asserted that in at least one embodiment, the first position 16 and the second position 17 are in substantial correspondence with the shaped and/or recessed portions 10r of the upper surface of the dispenser 10.

In an alternative embodiment, not shown in the attached figures, the seats 11 may take a shape of at least partially concave holding elements each one configured for holding a respective container 20 aligned along a substantially vertical direction and at a predetermined distance with respect to a surface of the dispenser 10 that is substantially accessible from above. This, as it will be better clarified by a subsequent reading of the present description, will allow to extract at least one support 30 from the container 20 starting from a bottom portion thereof, but will also allow to move the support 30 by substantially accessing the dispenser 10 from a higher position.

Figure 4:
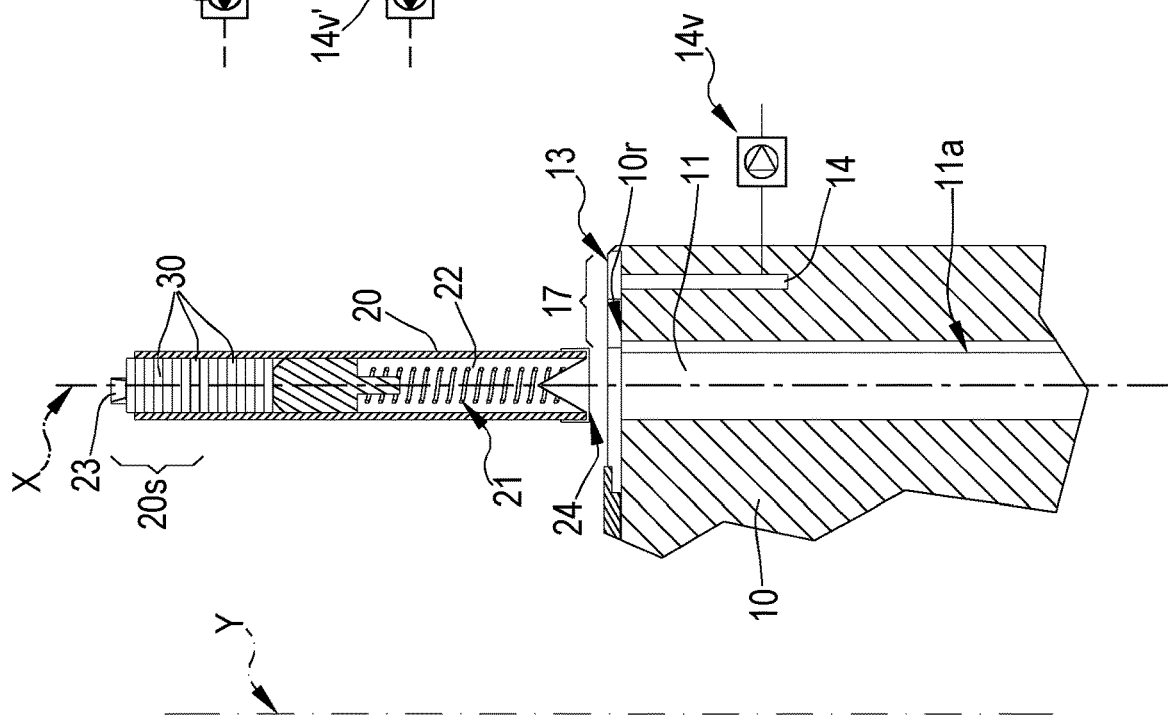
FIG. 4 shows a lateral sectional view of a dispenser suitable for containing a plurality of containers for impregnable or impregnated supports.

As it can be seen in FIG. 4, the container 20 has a substantially tubular body suitable for allowing the storage of a plurality of supports 30 in a stack. The body of the container 20, developing along a substantially axial direction, defines a supports unloading portion 20s that in use lies above the striking portion 24 and that substantially faces the upper surface of the dispenser 10. The supports unloading portion 20s is opposite with respect to the striking portion 24.

The supports 30, preferably discoidal in shape but not limited thereto, are stacked in the cavity 22 defined by the body of the container 20; said cavity 22 extends along a substantially axial direction. The supports 30 are pushed by a pusher which exerts on the plurality of supports 30 a force axially parallel to an axis of development of the container 20. The pusher is pushed by a spring 21 which is held in correspondence to the striking portion 24 of the container 20 and which is compressed to an increasing extent the more supports 30 are introduced into the cavity 22.

In correspondence with the supports unloading portion 20s the container 20 has at least one retainer 23 which partially obstructs the cavity 22 and which has an angled portion and arranged in such a way as to stop at least one support 30 which, pushed by the pusher, substantially exits from the tubular body of the container 20 and which can be extracted by pushing or pulling along a substantially oblique direction, in particular orthogonal, with respect to the direction of the push exerted by the pusher.

The device 1 herein described comprises an extractor 18 configured for performing a step of extraction of at least one support 30 from a first container 20, and for moving the support 30 between the first position 16 and the second position 17, which lie in correspondence of the upper surface of the dispenser 10. The extractor is installed on the supporting frame 100.

In use, there is a relative movement between the extractor 18 and the dispenser 10; the relative movement may be a rotational and/or a translational movement. In an embodiment, the extractor 18 is configured for simultaneously extracting a plurality of supports 30 from a respective plurality of containers 20.

As it can be seen in detail in FIG. 1 and FIG. 2, in a preferred embodiment, but non-limiting thereto, the extractor 18 comprises an extraction finger 18s movable at least between a first position radially internal with respect to the dispenser 10 and a second position radially external with respect to the dispenser 10.

Figure 3:
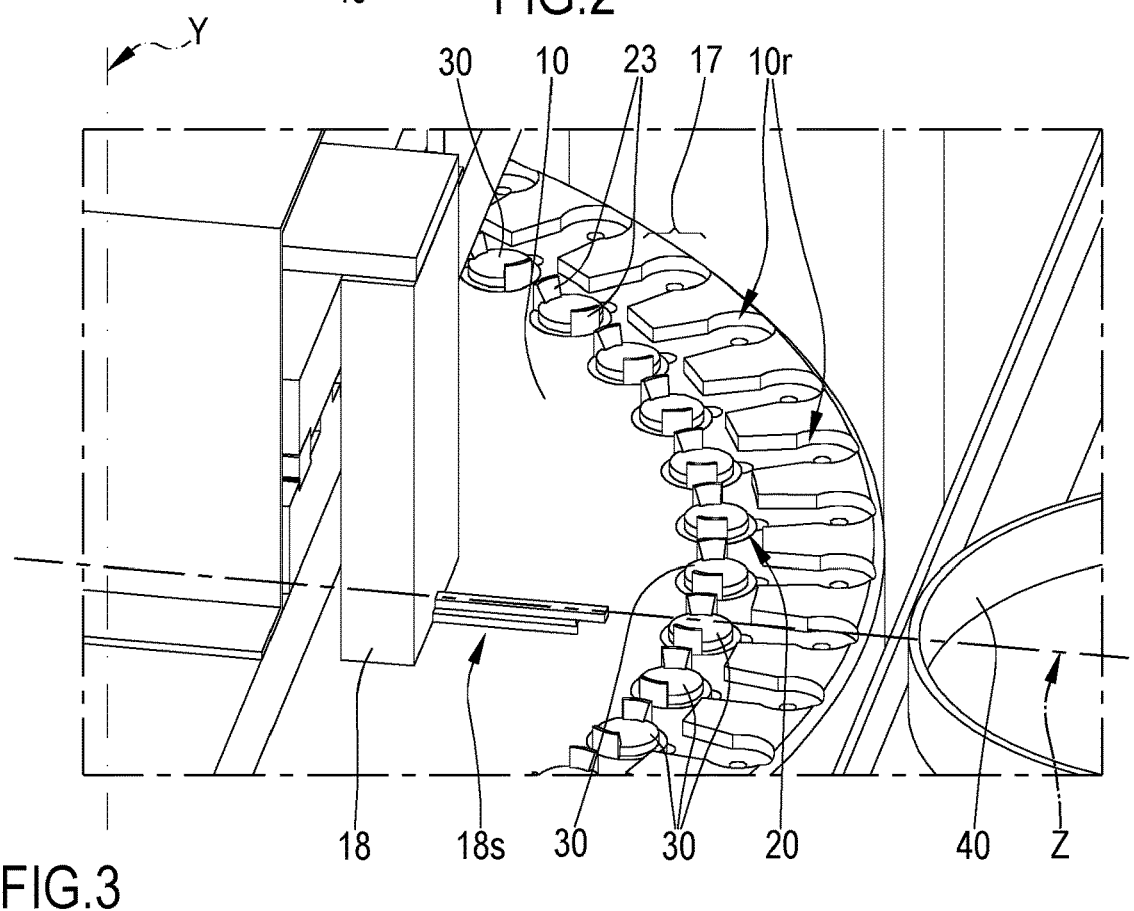
FIG. 3 shows a perspective view of a portion of the device object of the present disclosure.

The extraction finger 18s realizes the aforementioned pusher. As it can be seen from FIG. 3, the extraction finger 18s comprises a substantially stepped engagement portion detecting a recess upwardly delimited by a retaining wall and defining a pushing wall substantially oriented along a vertical plane that preferably, but not limited thereto, has a vertical extension at least equal to the thickness of the support 30 to be extracted or greater than the thickness of the support 30 to be extracted. Where the extraction finger 18s has to simultaneously extract a plurality of supports 30, the vertical extent of the pushing wall will preferably be equal to the number of supports to be extracted simultaneously.

For purposes of the present disclosure, the order of presentation (i.e., the order of extraction) of the supports 30 from the respective container 20 determines the nomenclature "first", "second", and so on, for the respective support 30. Thus, a first container 20 will have a first support 30 (in use the first to be extracted) stacked on a second support 30 (in use, the second to be extracted), and so on. A second container 20 will have a first support 30 (in use, the first to be extracted), stacked on a second support 30 (in use, the second to be extracted), and so on.

In the embodiments shown in the figures, the movement of the extraction finger 18s is a substantially axial translation along a movement axis Z radial with respect to the center of the dispenser 10. In use, during the translation, the extraction finger 18s moves from the first radially internal position to the second radially external position and, being at substantially the same height at which the support 30 is located, engages at least one support 30 from the container 20; at this point, the support 30 is still substantially in the first position 16. After the engagement, the support 30 is extracted from the first container 20, retained in a fixed position in the respective seat, and is dragged in substantial sliding within the shaped and/or recessed portion 10r along the movement axis Z, moving from the first position 16 to the second position 17 being pushed by the extraction finger 18s.

In an alternative configuration, not shown in the attached figures, the extraction finger 18s may be configured for extracting the support 30 from the container 20 by means of a traction towards a direction radially external with respect to the center of the dispenser 10. In such a case, in use, during the translation the extraction finger 18s moves from the first radially internal position towards the second radially external position and engages at least one support 30 from the container 20; at this point the support 30 is substantially still in the first position 16. After the engagement, the support 30 is dragged in substantial sliding within the shaped and/or recessed portion 10r along the movement axis Z, moving from the first position 16 to the second position 17 being pulled by the extraction finger 18s. The extraction by traction may also occur along a radially internal direction.

In correspondence of the second position 17, on the upper surface of the dispenser 10 there is, and opens, a holding hole 14, which is connected to a first vacuum holder 14v configured for drawing air from the upper surface of the dispenser 10 through the holding hole 14. A vacuum pump is operatively connected with a first vacuum holder 14v.

In particular, the holding hole 14 is positioned within the shaped and/or recessed position and extends along an at least partially vertical direction. The area around the holding hole 14 acts as a striking surface when the vacuum is exerted on the bottom surface of the support 30.

When a support 30 arrives in correspondence of the holding hole, it is held by means of a vacuum. In this way, it is ensured that a precise position of the support 30 is maintained.

It is noted that the presence of the vacuum holder is not necessarily linked to the presence of all the above-described technical features, since the Applicant has in particular conceived an embodiment of the device 1 which comprises:
- a dispenser 10, provided with a plurality of seats 11 configured for housing a corresponding plurality of containers 20, each one containing a plurality of supports 30 impregnable and arranged in a stack;
- an extractor 18, positioned in substantial correspondence of the dispenser 10 and/or operatively associated with the dispenser 10 and configured for extracting at least one first support 30 from a first container 20 housed in a respective seat 11 of the dispenser 10, and for moving the first support 30 between a first position 16 within the first container 20 and a second position 17 extracted from the first container 20;
- a collector 19, configured for collecting the first support 30 from the second position 17 and for transporting the first support 30 from the second position 17 towards a culture plate 40;

and wherein the device 1 comprises at least one first vacuum holder 14v configured for creating a vacuum between a striking surface and the first support 30, wherein the vacuum holder is configured for holding the at least one first support 30 in substantial correspondence of the second position 17 and/or of the collector 19.

Two contiguous shaped and/or recessed portions 10r will have a respective holding hole 14, each one operationally connected to the first, and respectively second, vacuum holder.

The striking surface may be the upper surface of the dispenser 10, in particular in correspondence of the shaped and/or recessed portion 10r, or a surface of the dispenser 10 accessible from above, or—as it will be better clarified in the following portion of the description—a collection area of an auxiliary dispenser 10w.

The dispenser 10 rotates around its central axis with a controlled rotation set by an automatically controlled rotor, so that a second seat 11 is positioned in a position such that to allow the extraction of a further support 30 from a second container 20. In use, therefore, a first step of extraction of a first support 30 from the first container 20 is followed by a step of extraction of a first support 30 from the second container 20. In fact, in a non-limiting embodiment, the dispenser 10 is a rotatable dispenser, the rotation of which is controlled by a rotor preferably installed below the bottom surface of the dispenser 10. The data processing unit controls the actuation of the rotor so as to allow said controlled rotation. In particular, it is noted that the rotation may be clockwise or counter clockwise.

After the rotation of the dispenser 10, the device 1 is configured for performing a movement of the extraction finger 18s in the form of a substantially axial translation along a movement axis Z radial with respect to the center of the dispenser 10. In use, during the translation, the extraction finger 18s moves from the first radially internal position towards the second radially external position and engages at least one support 30 from the container 20; at this point, the support 30 is substantially still in the first position 16. After the engagement, the support 30 extracted from the second container 20 is dragged in substantial sliding within the shaped and/or recessed portion 10r moving from the first position 16 to the second position 17 being pushed by the extraction finger 18s. A further creation of the vacuum allows the appropriate holding of the support 30 extracted from the second container 20.

Alternatively to the above, in an alternative embodiment, the dispenser 10 is kept in a fixed position, and it is the extractor 18 that rotates, in use, with respect to the dispenser 10 to first extract a first support 30 from the first container 20 along said radially external direction and, subsequently to extract a first support 30 from the second container 20 along said radially external direction after a rotation of the extractor finger by an angle sufficient to position itself in correspondence of the second seat 11.

Still, in an alternative embodiment, the extractor 18 may be configured for simultaneously extracting a first support from a first container 20 and a first support 30 from a second container 20. This is possible both in the case where it is the dispenser 10 that rotates relative to the extractor 18, and in the case where it is the extractor 18 that rotates with respect to the dispenser 10, this time fixed.

Figure 5:
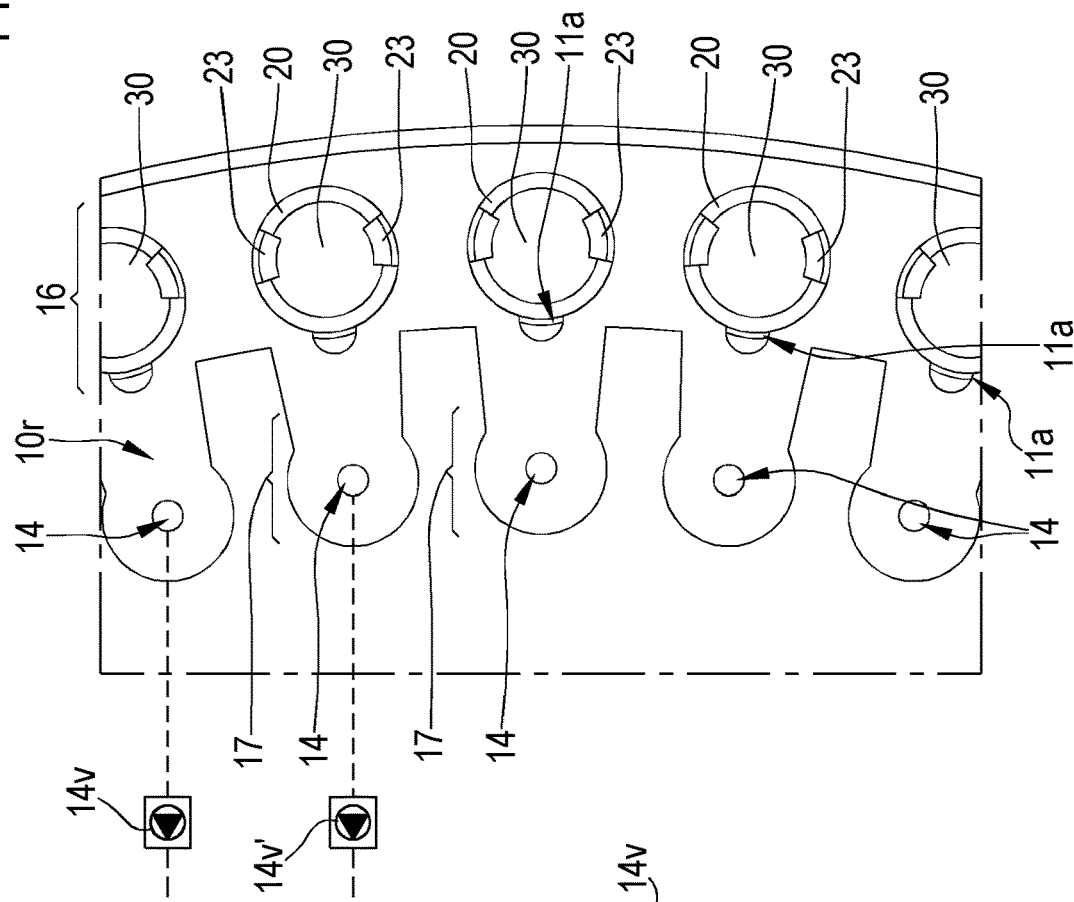
FIG. 5 shows a detailed view of a portion of a dispenser of the device object of the present disclosure.

As it is shown in FIG. 5, the Applicant has conceived an alternative embodiment form for the dispenser 10, wherein the plurality of seats 11 suitable for housing, each one, a container 20 is arranged on an ideal circumference radially external with respect to the ideal circumference in correspondence to which the upper surface portions intended to temporarily retain at least one respective support 30 extracted from the container 20 are positioned. In such a case, the first position 16 is radially outermost with respect to the second position 17. The embodiment of the dispenser 10 of FIG. 5 may be associated with an extractor 18 whose extraction finger 18s is configured for working pushing or, alternatively pulling, thus pushing or pulling the support 30. The Applicant believes that the description of these two working modes for the extractor 18 has been previously exhaustively described, and for this reason does not repeat the description of them again herein, referring the reader to the preceding paragraphs. However, unlike previous embodiments in which the movement of the at least one first support 30 takes place along a radially external direction, in case of the embodiment of FIG. 5, this movement occurs along a radially internal direction of movement.

A collector 19 is configured for collecting the support 30 from the second position 17 and for transporting the support 30 from the second position 17 towards a culture plate 40. FIGS. 6 through 9 show successive steps of a movement of the collector 19 to perform the transportation of the support 30.

Figure 6:
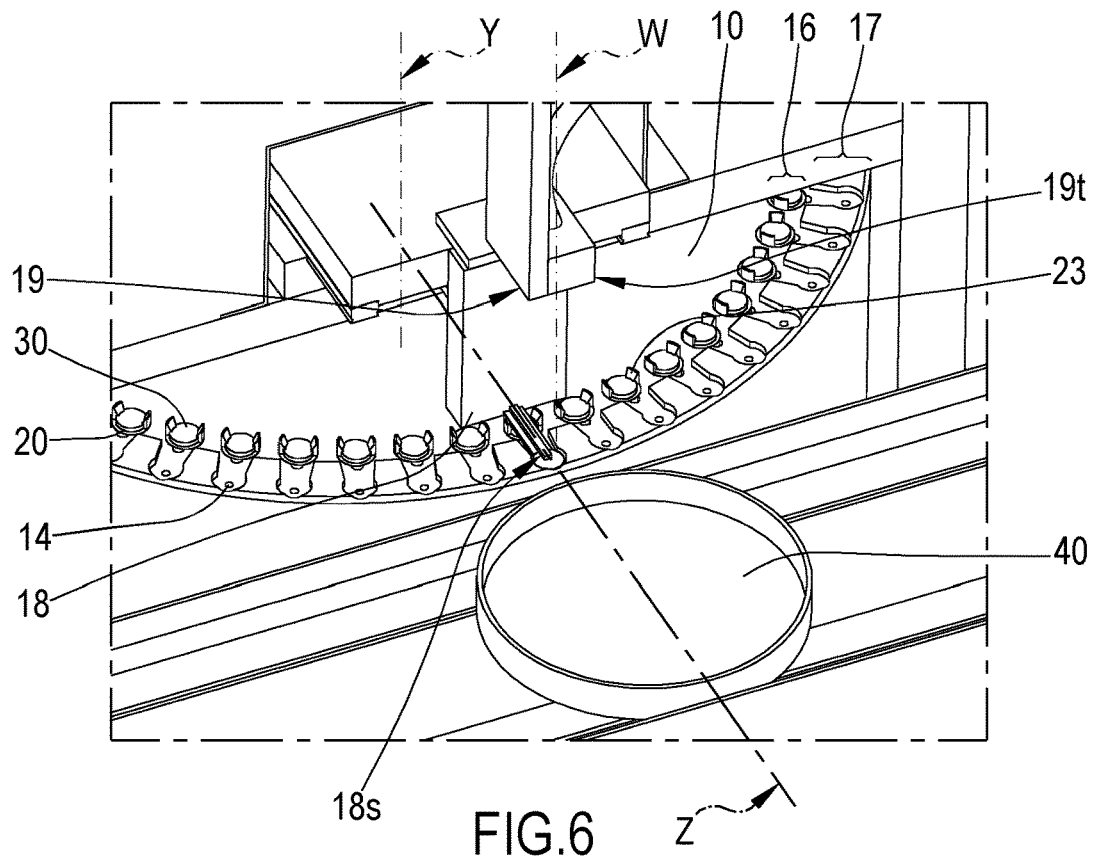
FIG. 6 shows a perspective view of a portion of the device object of the present disclosure, in a configuration wherein a collector is about to collect an impregnated support from the dispenser.

FIG. 6 shows a perspective view of a configuration wherein the collector 19 is in the process of extracting a support 30 from the dispenser. In FIG. 6, the extraction finger 18s is in the second radially external position, and has pushed a support 30 in correspondence of the holding hole so that said support 30 is retained by means of the vacuum. In fact, it should be noted that in correspondence of the extraction finger indicated by the numerical arrow reference 18s, the shaped and/or recessed portion at the holding hole is not shown, and this is a sign that the support 30 is in the second position 17.

The collector 19 is axially aligned above the dispenser 10 and, in particular, is axially aligned above the second position 17 in correspondence of which is located the support 30 that has been pushed by the extraction finger 18s. The first conveyor belt 50 has been moved so that the culture plate 40 is in substantial correspondence of the dispenser 10 and, in particular, is aligned with the axis Z which radially departs from the center of the dispenser 10 passing through the first position 16 and the second position 17, in particular passing through the center of the seat 11 and the center of the holding hole 14. As it can be seen from FIG. 6, the culture plate 40 is empty.

Figure 7:
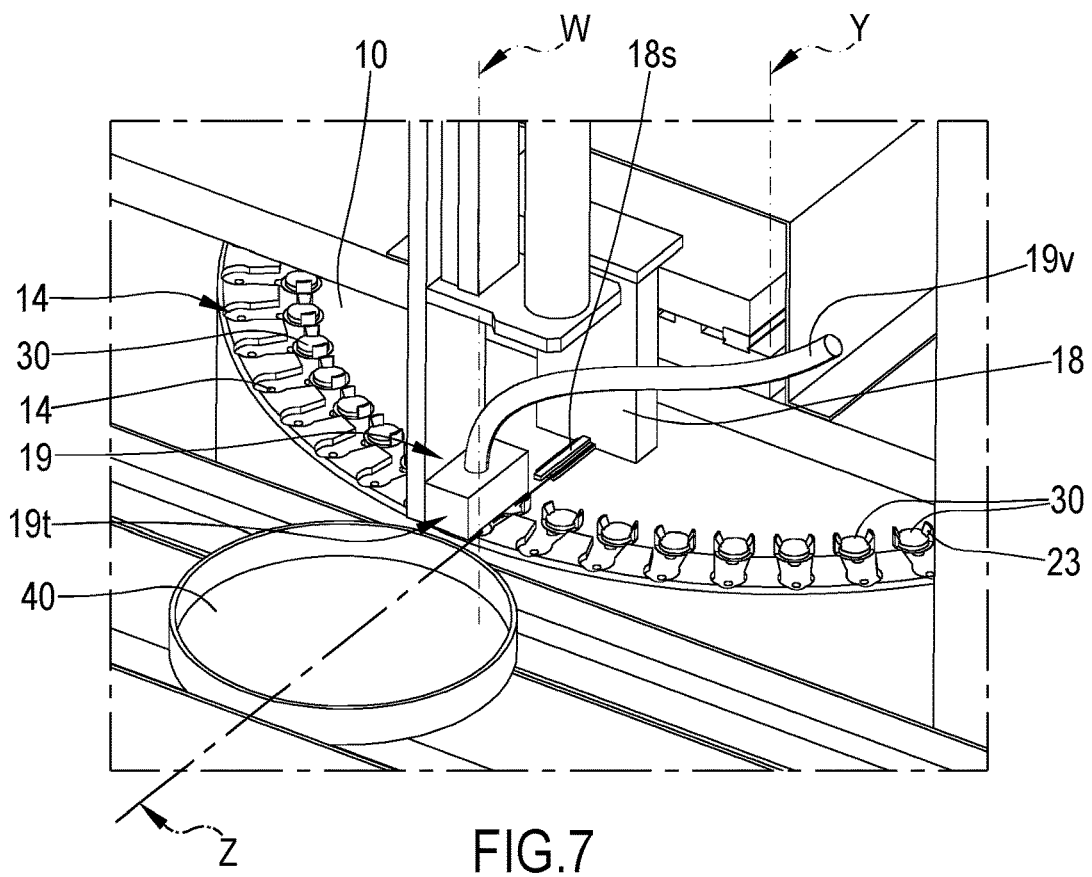
FIG. 7 shows a perspective view of a portion of the device object of the present disclosure, in a configuration wherein a collector has collected the support impregnated from the dispenser and moves towards depositing it in a culture plate.

As shown in FIG. 7, subsequently the collector 19 performs an axial translation movement along the axis W, substantially vertical, in order to approach, accessing from above, the dispenser 10 so as to be able to collect the support 30 from the second position 17. In detail, when it is arrived in correspondence of the second position 17, and in particular having a collection head 19t in substantial contact with the support 30, an auxiliary vacuum holder is activated to exert a vacuum between an upper surface of the support 30 and the collector 19, so that the support 30 can be firmly retained in substantial correspondence of a lower end portion of the collection head 19t. This vacuum is sufficient to lift the support 30 from the shaped and/or recessed portion 10r. Thus, the device 1 comprises an auxiliary vacuum holder 19v operatively connected to the collection head 19t, which allows the holding of the support 30 for a predetermined period of time in correspondence of the collection head 19t.

The auxiliary vacuum holder comprises at least one duct operatively connected to said vacuum pump and comprises a hole opening on the lower end portion of the collection head 19t. Said lower end portion of the collection head 19t may have a substantially planar configuration or, alternatively, may be provided with a recess whose shape is preferably tracing that of the support 30.

In substantial correspondence of the instant of time in which the auxiliary vacuum holder 19v is activated, the first vacuum holder 14v operatively connected with the holding hole 14 on the dispenser 10 is deactivated, or otherwise placed in a configuration such that a vacuum is no longer exerted between the dispenser 10 and the support 30. For this reason, it may therefore be understood that the activation of the first vacuum holder 14v and of the auxiliary vacuum holder is alternative. The data processing unit controls the alternation of the activation and deactivation of the first vacuum holder 14v and of the auxiliary vacuum holder.

In order to allow an effective extraction of the support 30, when the collector 19 performs the aforementioned translational movement along the axis W, the extraction finger 18s is retracted to a position radially internal with respect to the dispenser 10; this configuration is well shown in FIG. 7.

Subsequently, the collector 19 is raised through an axial translation movement along the axis W and then axially translated along a direction substantially parallel to the axis Z that radially departs from the center of the dispenser 10.

The translation of the collector along the aforementioned direction is such that it radially departs from the center of the dispenser 10. The vacuum is kept during the raising along the axis W and the translation along the direction substantially parallel to the axis Z so that the support 30 can be firmly retained in substantial correspondence of an upper surface thereof on the collection head 19t of the collector 19.

Figure 8:
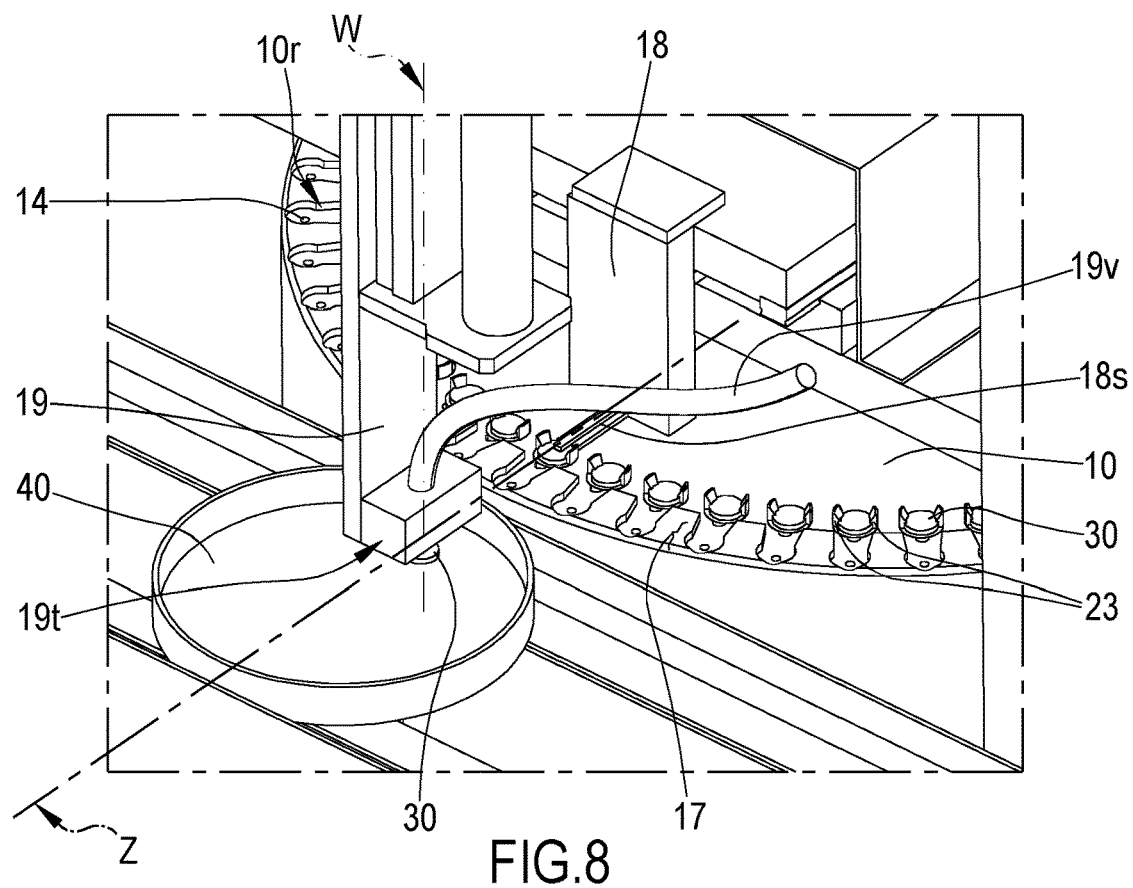
FIG. 8 shows a perspective view of a portion of the device object of the present disclosure, in a configuration wherein the collector is in substantial axial alignment upon the culture plate and is about to deposit the impregnated support on the culture plate.

In FIG. 8 is shown a subsequent step wherein the collector 19 is in substantial axial alignment above the culture plate 40 and retains the support 30 by means of the previously created vacuum. In particular, FIG. 8 shows a configuration wherein the collector 19 is at a height such that it brings the support 30 into substantial contact with the culture plate 40. At this point, the vacuum is released by means of a deactivation of the pump or closing of the valve of the collector 19. The support 30 is now deposited on the culture plate 40.

Figure 9:
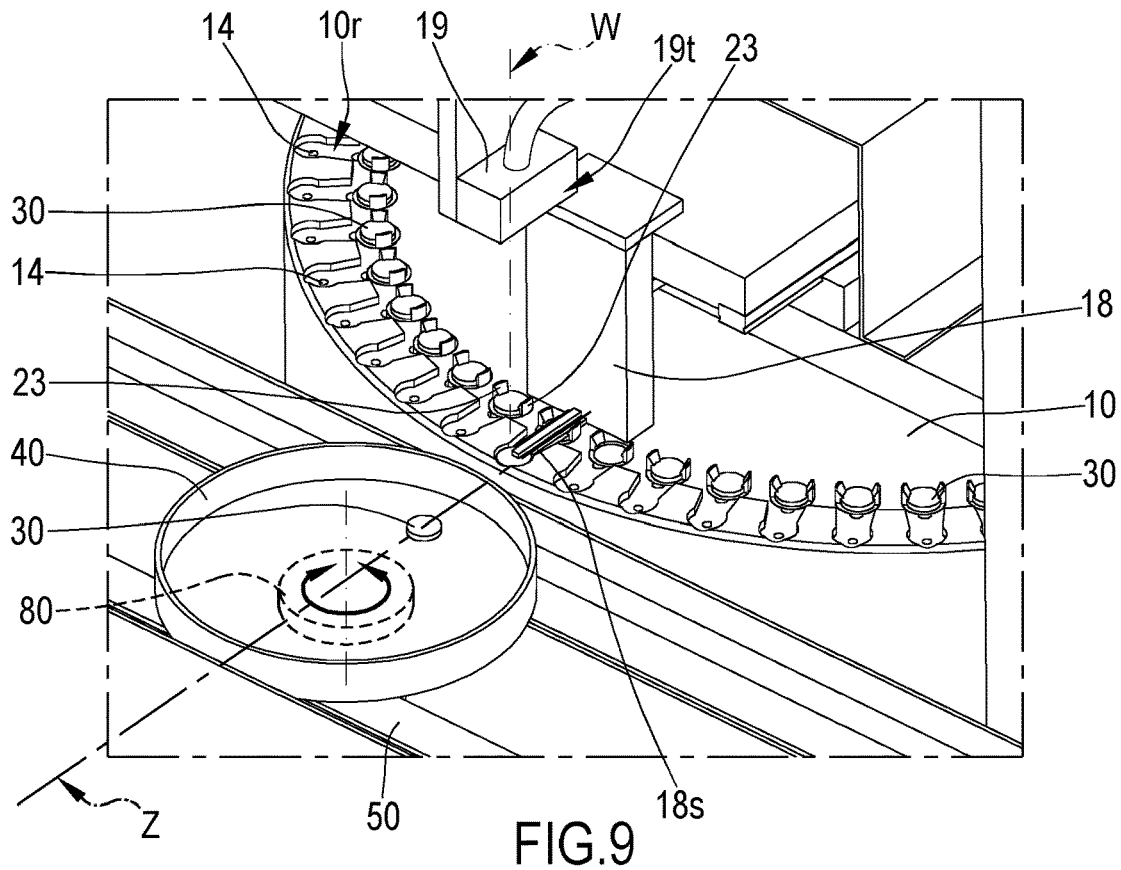
FIG. 9 shows a perspective view of a portion of the device object of the present disclosure, in a configuration wherein the collector has deposited the impregnated support on the culture plate, and is axially aligned upon the dispenser for collecting another impregnated support.

At this point, as it is shown in FIG. 9, the collector 19 is raised by means of an axial translation movement along the axis W and then axially translated along a direction substantially parallel to the axis Z, in particular radially approximating the center of the dispenser 10 until it reaches a substantial alignment with the second position 17. FIG. 9 shows a configuration in which the dispenser 10 has been rotated in a counter clockwise direction by means of a rotation set by the data processing unit on the rotor. With such a rotation, a new support 30 can be extracted from another container 20. In fact, it can be observed from FIG. 9 that the container 20 which is on the right of the collector 19 is empty. In particular, in FIG. 9 the device 1 is shown in a particular instant of time of its working cycle in which the extraction finger 18s has already been moved in a radially external direction along the axis Z in order to push a new support 30 (i.e., the first support 30 of a second container) from the first position 16 to the second position 17.

In order to allow a deposit of a new support 30 on the culture plate 40, this culture plate 40 must be rotated. A rotor disk 80, positioned below the culture plate 40, or alternatively a rotating prehension device, perform a controlled rotation of the culture plate 40 around a substantially vertical axis. The rotor disk 80 or the rotating prehension device are controlled by the data processing unit. The rotor disc 80 or the rotating prehension device may be moved away from and/or approaching the culture plate 40, so that it is possible a release of the culture plate 40 for subsequent movements.

Figure 10:
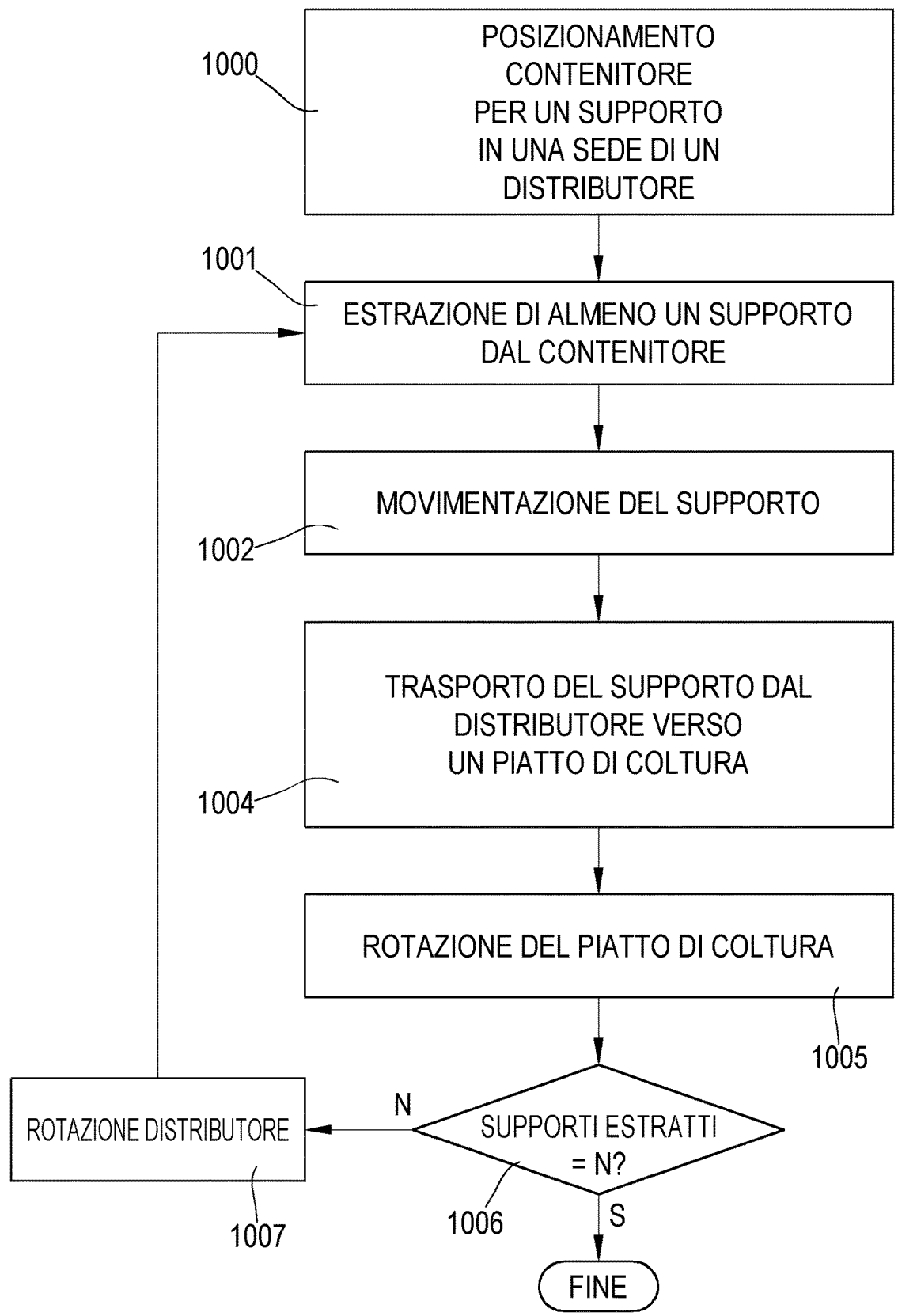
FIG. 10 shows a flow chart of a method for the distribution of impregnable or impregnated supports according to a first non-limiting embodiment.

FIG. 10 shows a flowchart summarizing the functioning of the device 1 according to Figures from 6 to 9; in detail, the block 1000 identifies the positioning of at least a first container 20, containing a plurality of supports 30 arranged in a stack, in a first seat 11 of a rotatable dispenser 10. If the dispenser 10 possesses a plurality of seats 11 as in the case of the non-limiting embodiment shown in Figures from 6 to 9, there will be further steps of positioning of a second, or more, container(s) in a respective seat 11 of the dispenser 10.

The aforementioned positioning (block 1000) may be performed manually by an operator or, alternatively, may be performed by a servo actuator of the device 1. Thus, in an embodiment, the step of positioning of the at least one first container 20 is controlled by a data processing unit, in particular by a data processing unit of the device 1.

In a non-limiting embodiment, the positioning of the container 20 in the seat 11 comprises the introduction of it along an axial direction substantially aligned with the direction along which the seat 11 is developed. In the case of the embodiment shown in the attached figures, the direction of the introduction of the container 20 is substantially vertical.

In a particular embodiment, the positioning of the container 20 in the seat 11 causes the supports unloading portion 20s of the first container 20 to face upwards and substantially face the upper surface of the dispenser 10, such that a support 30 faces at a height substantially aligned with the height at which the shaped and/or recessed portion 10r lies. In a further embodiment, the different location of the seats 11 causes the supports 30 unloading portion of the first container 20 to face downwards, and still face on the upper surface of the rotatable dispenser.

Once the filling—partial or total—of the seats 11 with a respective container has been completed, a step of extraction of at least one support 30 from one of the containers 20 present in the dispenser 10 may take place. Such step of extraction is schematically represented by the block 1001 of FIG. 10.

The extraction of the support 30 firstly comprises the activation of the extractor 18 and comprises, after said activation, a movement of the support 30 between the first position 16 and the second position 17, in particular where the first and second position 16, 17 lie substantially in correspondence of the surface of the dispenser 10. The movement is represented by the block 1002 of the diagram of FIG. 10. More generally, the movement of the support 30 takes place between said first position 16 and said second position 17 where at least one between the first position 16 and said second position 17 lies substantially in correspondence of a height comprised between at least half of the vertical development of the dispenser 10 and a height substantially corresponding to the height at which the upper surface of the dispenser 10 is located and/or wherein the first position 16 and the second position 17 are accessible from a direction substantially inclined with respect to a direction of extraction of the support 30, in particular being accessible from above, and face the outside of the dispenser 10.

The Applicant particularly observes that the step of extraction (block 1001) of the support 30 from the container 20 is followed by the movement (block 1002) because in at least one alternative and non-limiting embodiment, the movement realized by the extractor 18 to cause the extraction of the support 30 from the container 20, by specific construction of the support 30, the container 20 and/or by conformation or direction of orientation of the seat 11, may imply a movement significantly distinguishable with respect to the nearly linear translation of the support 30 realized by means of the extractor finger 18s in the embodiment represented in Figures from 6 to 9.

After the motion of the holder 30, a step of transportation of the support 30 from the dispenser 10 toward a culture plate 40 takes place; this step of transportation is identified by the block 1004 in FIG. 10. There is a step of actuation of the collector 19 to collect the support 30 from the second position 17 and a step of transportation, described above, performed by the collector 19, to transfer the support 30 from the dispenser 10 to the culture plate 40.

The block 1005 identifies a step of rotation of the culture plate 40 to allow a new deposition of a new support 30. The rotation of the culture plate 40 is preferably controlled by a data processing unit of the device 1. The device 1 is configured for extracting a predefined number N of supports from the dispenser 10 to deposit them on the culture plate 40. For example, such predefined number N may be equal to the number of supports that may be supported on the culture plate 40. The device 1 herein described is preferably configured for checking (block 1006) whether the number of supports 30 extracted from the dispenser 10 is equal to N.

In affirmative case (output S of block 1006), the operational cycle of extraction of supports 30 from the dispenser 10 ends and the culture plate can be translated towards the target position through the first and/or second conveyor belt 50, 60.

In negative case (output N of block 1006), the operational cycle of extraction of supports 30 from the dispenser continues and (block 1007) a rotation of the dispenser 10 takes place so that a subsequent container 20 (or equivalently a further seat 11), be in a predefined position intended to allow the extraction of the at least one support 30 from the subsequent container 20 by means of the extractor 18.

Figure 11:
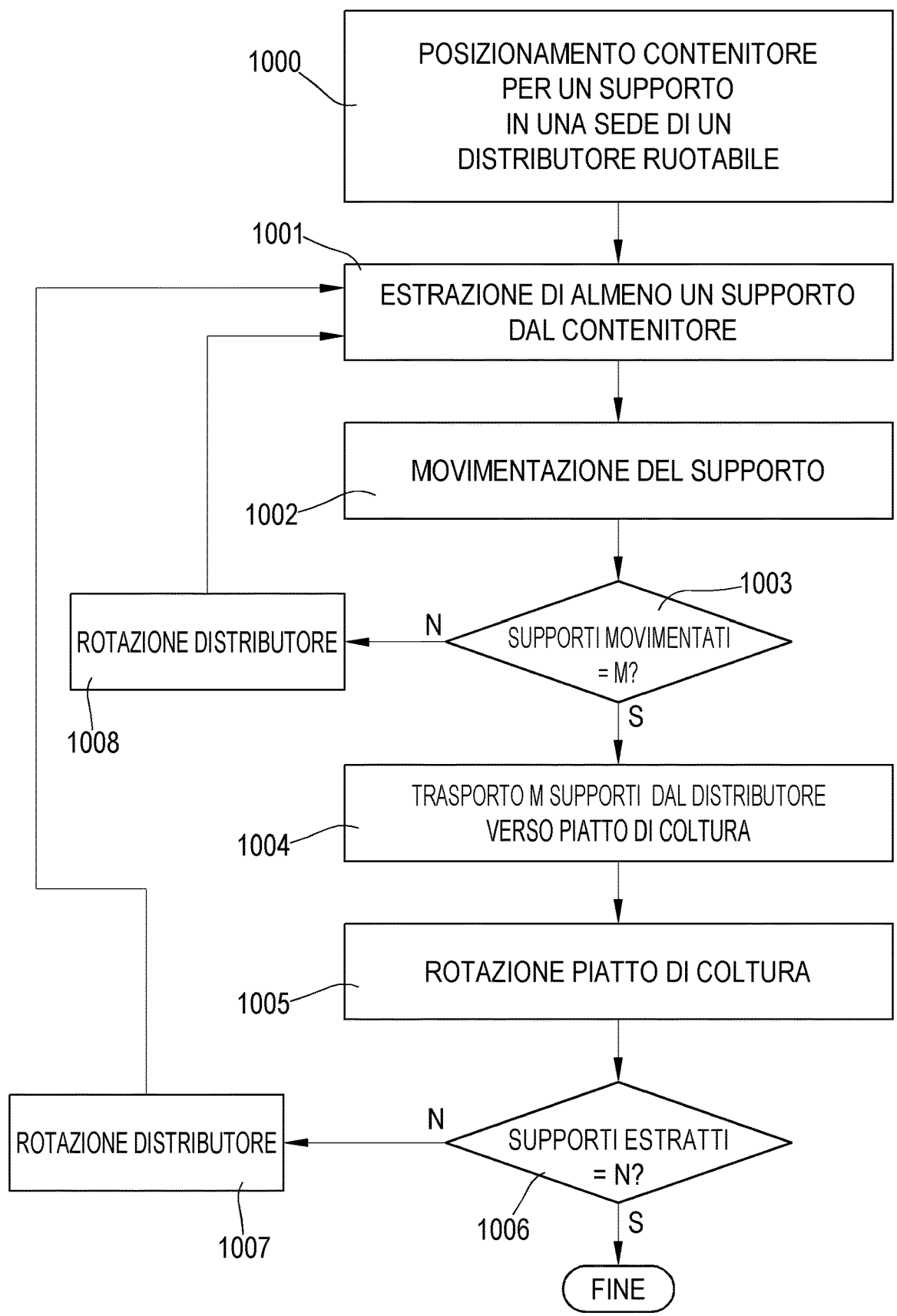
FIG. 11 shows a flow chart of a method for the distribution of impregnable or impregnated supports according to a second non-limiting embodiment.

The block diagram of FIG. 11 shows an operating cycle of an alternative embodiment for the device 1 herein described. Also in this embodiment, the block 1000 identifies the positioning of the at least one first container 20, containing a plurality of supports 30 arranged in a stack, into a first seat 11 of a rotatable dispenser 10. If the dispenser 10 possesses a plurality of seats 11 as in the case of the non-limiting embodiment shown in Figures from 6 to 9, further steps of positioning of a second, or more, container(s) into a respective seat 11 of the dispenser 10 will be present.

In a non-limiting embodiment, the positioning of the container 20 in the seat 11 comprises the introduction thereof along an axial direction substantially aligned with the direction along which the seat 11 itself is developed. In the case of the embodiment shown in the attached, the direction of introduction of the container 20 is substantially vertical.

Once the filling—partial or total—of the seats 11 with a respective container has been completed, a step of extraction of at least one support 30 from one of the containers 20 present in the dispenser 10 may take place. This step of extraction is schematically represented by the block 1001 of FIG. 10.

The extraction of the support 30 firstly comprises the activation of the extractor 18 and comprises, after said activation, a movement of the support 30 between the first position 16 and the second position 17, in particular where the first and second position 16, 17 lie substantially in correspondence of the surface of the dispenser 10. The movement is represented by the block 1002 of the diagram of FIG. 9. More generally, the movement of the support 30 takes place between said first position 16 and said second position 17 where at least one between said first position 16 and said second position 17 lies substantially in correspondence of a height comprised between at least half of the vertical development of the dispenser 10 and a height substantially corresponding to the height at which there is the upper surface of the dispenser 10 and/or wherein the first position 16 and the second position 17 are accessible from above and face the outside of the dispenser 10.

Again, the Applicant particularly observes that the step of extraction (block 1001) of the support 30 from the container 20 comprises the movement (block 1002) because in at least one alternative and non-limiting embodiment, the movement realized by the extractor 18 to cause the extraction of the support 30 from the container 20, by specific construction of the support 30, of the container 20 and/or by conformation or direction of orientation of the seat 11, may imply a movement significantly distinguishable with respect to the nearly linear translation of the support 30 realized by the extractor finger 18s in the embodiment represented in Figures from 6 to 9.

The device 1 is configured for causing the movement of a plurality of supports 30 from the first position 16 to the second position 17 before proceeding with the transportation of the supports so moved toward the culture plate 40. In particular, the device 1 is configured for causing a movement of a predetermined number M of supports 30 from the first position 16 to the second position 17 before proceeding with transporting the M supports 30 so moved toward the culture plate 40.

For this reason, block 1003 identifies a step of checking whether the number of supports 30 moved from the first position 16 to the second position 17 is equal to M.

In negative case (block 1003, output N), a rotation of the dispenser 10 is performed (block 1008), so that a new container 20 (or equivalently a new seat 11), is in a predefined position intended to allow the extraction of the at least one support 30 from the next container 20 by means of the extractor 18.

In affirmative case (block 1003, output S), a step of transportation of the at least one support 30 from the dispenser 10 toward a culture plate 40 is performed; this step of transportation is identified by block 1004 in FIG. 10. There is a step of actuating the collector 19 to collect the at least one support 30 from the second position and a step of transportation, described above, performed by said collector 19 to transfer the support 30 up to the culture plate 40.

In particular, it is noted that the expression "transportation of the at least one support 30" implies that in one embodiment the collector 19 is operated to collect a support 30 from the second position, and lay it on the culture plate 40, and again return in a position of substantial axial alignment to a second position 17 to collect a subsequent support 30.

In this case, the dispenser 10 is again rotated by its rotor to allow the access of the collector 19 to a second position 17 contiguous with that from which the support 30 deposited on the culture plate 40 was collected. After each new deposition of a support 30 on the culture plate 40, the latter is rotated with a controlled rotation. Alternatively, the dispenser 10 may be kept in a determined and fixed position while the collector 19 performs a plurality of cycles of collection and subsequent deposition of supports 30 onto the culture plate 40. In the latter case, however, the collector 19 will be configured for performing a composite movement wherein the horizontal translation cannot be longer merely axial along a direction radial with respect to the center of the dispenser 10, but must be a horizontal translation along a direction substantially inclined with respect to said radial direction to reach, at each collection cycle, a second position 17 different from the previous one, until a number M of supports movement cycles is reached. Still alternatively, the collector 19 may be configured for performing a translational movement along a direction radial with respect to the center of the dispenser 10, and for performing a rotation sufficient to position itself in a plurality of second positions 17 for the collection of the supports 30. It thus appears clear that the movement executable by the collector 19 is a composite movement.

In an alternative embodiment, the collector 19 is actuated to simultaneously collect a plurality of supports 30 from a plurality of second positions 17 on the dispenser 10 and then deposit said plurality of supports 30 on the culture plate 40.

The block 1005 identifies a step of rotation of the culture plate 40 to allow a new deposition of a new support 30 collected from the dispenser 10, on said culture plate 40.

The device 1 is configured for extracting a predefined number N of media from the dispenser 10 to deposit them on the culture plate 40. For example, said predefined number N may be equal to the number of supports that may be supported on the culture plate 40. Preferably, the device 1 described herein is configured for checking (block 1006) whether the number of supports extracted from the dispenser 10 is equal to N.

In affirmative case (output S of block 1006), the operational cycle of extraction of supports 30 from the dispenser 10 ends and the culture plate may be translated towards the target position by the first and/or second conveyor belt 50, 60.

In negative case (output N of block 1006), the operational cycle of extraction of supports 30 from the dispenser continues and (block 1007) a rotation of the dispenser 10 takes place, so that a new container 20 (or equivalently a new seat 11), is in a predefined position intended to allow the extraction of the at least one support 30 from the next container 20 by means of the extractor 18. In particular, it is noted that in the case where the collector 19 is configured for simultaneously collecting a plurality of M supports 30, the rotation of the dispenser 10 occurs for an M number of "jumps" in order to reach an M-th second position 17, or equivalently, an M-th contiguous seat 11.

Figure 12:
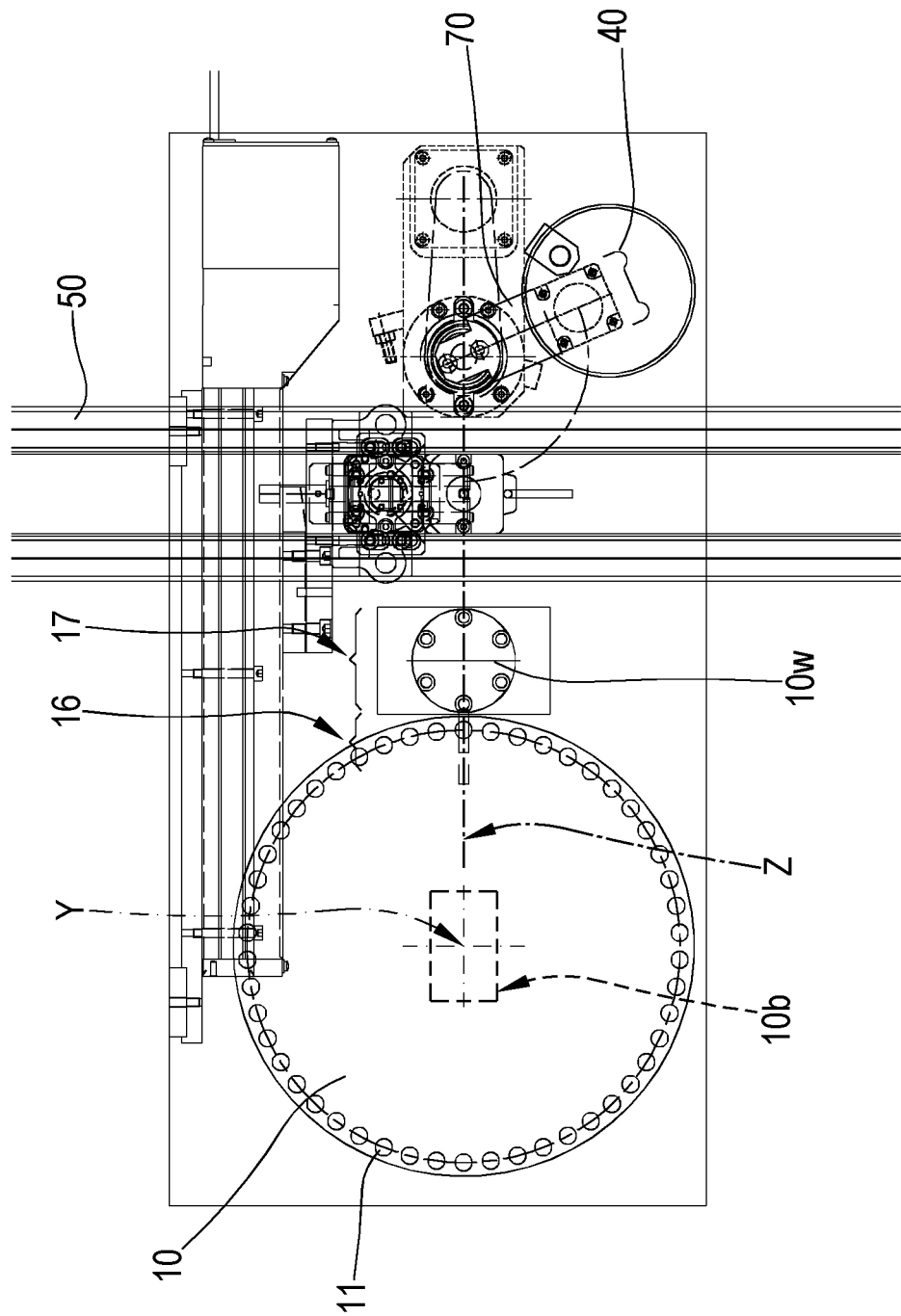
FIG. 12 shows a top view of an alternative embodiment of the device object of the present disclosure.

An alternative embodiment of the device 1 is shown in FIG. 12. In this embodiment, it is observed the presence of only one conveyor belt 50 and a translator which transports the culture plate 40 from a starting position to the conveyor belt by means of a rotational movement around a sensibly vertical axis and/or substantially parallel to the axis Y.

In the embodiment of FIG. 12, the dispenser 10 comprises a plurality of seats 11 arranged in a substantially perimeter outer position and opening on the upper surface. Preferably, such holes are aligned along a direction substantially inclined with respect to the plane on which the upper surface of the dispenser 10 lies; in the embodiment shown in the figures, the seats 11 extend axially along a substantially vertical main development axis and orthogonal with respect to the upper surface of the dispenser 10. Preferably, each seat 11 comprises a slotted portion 11a axially extending for at least part of, optionally substantially all of, the extension of the seat 11 along the main development axis.

In contrast to the embodiment previously shown, in the embodiment of FIG. 12, the second position 17 wherein the support 30 is retained before being transported on the culture plate 40 is not on the dispenser 10 but is on an auxiliary dispenser 10w, which is mounted on the supporting frame 100 and has a plurality of collection areas 10r preferably arranged in a substantially perimetral outer position and are on the upper surface of the auxiliary dispenser itself. In the embodiment of FIG. 12, this auxiliary dispenser 10w has a substantially circular shape. This should not be understood in a limiting way, since the auxiliary dispenser 10w may assume a plurality of different shapes, for example and in a non-limiting extent rectangular.

The upper surface of the auxiliary dispenser 10w is substantially planarly aligned with the upper surface of the dispenser 10 (in particular, there is an alignment on a substantially identical horizontal plane) so that a movement of the element 30 extracted from the container 20 can be realized by substantially sliding on the upper surface of the dispenser 10, starting from a first position 16, to reach the upper surface of the auxiliary dispenser 10w. In correspondence of said collection areas 10r, the auxiliary dispenser 10w comprises respective holding holes 14, preferably in a number equal to one for each collection area 10r, which allow to create a vacuum with the lower surface of the support 30 when positioned in correspondence of the area itself.

Figure 14:
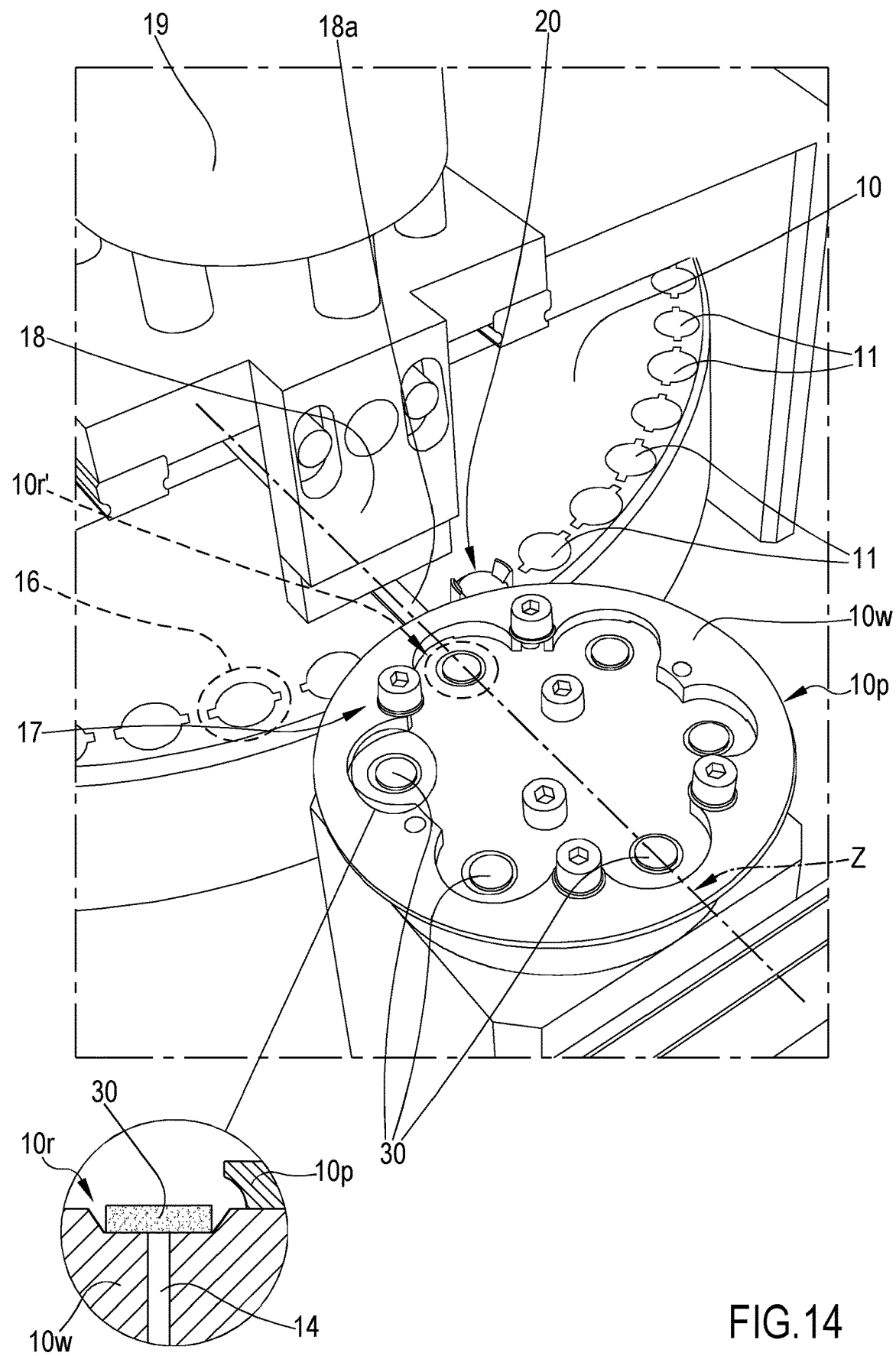
FIG. 14 shows a detailed view of the device in the embodiment of FIG. 12.

The auxiliary dispenser 10w is movable; in the specific embodiment visible in FIG. 12 and FIG. 14, the auxiliary dispenser 10w is rotating, and rotates around an axis substantially vertical and parallel to the axis Y. The axis of rotation of the dispenser 10 and the axis of rotation of the auxiliary dispenser 10w are therefore parallel. The rotation of the auxiliary dispenser 10w is synchronized with the rotation of the dispenser 10 so that a determined collection area 10r' of the upper surface of the auxiliary dispenser 10w is radially aligned with a certain seat 11 of the dispenser 10.

In a preferred, but non-limiting, embodiment, the auxiliary dispenser 10w is placed in rotation by its own rotor which is operatively connected with a data processing unit of the device 1 which also controls the rotation of the dispenser 10. Alternatively, there may be a single rotor for the auxiliary dispenser 10w and for the dispenser 10, which transmits a rotational motion to both the auxiliary dispenser 10w and the dispenser 10 by means of rotation demultiplying means (gears, belt drives on pulleys of suitable radius).

In this case, in use, the extraction finger 18s during its movement between the position radially internal with respect to the center of the dispenser 10 and the position radially external with respect to the center of the dispenser pushes the support 30 from the first position 16 (on the upper surface of the dispenser 10) to the second position 17 of the collection area 10r' of the auxiliary dispenser 10w.

In particular, a non-limiting embodiment of the auxiliary dispenser 10w is shown in FIG. 14, which has a perimeter ring 10p that identifies a substantially central daisy-shaped hole, having a plurality of recesses each one defining a convexity facing the radially outermost portion of the auxiliary dispenser 10w. The number of recesses is equal to the number of collection areas 10r, and each recess lies substantially in correspondence of a respective collection area 10r'. In a preferred, non-limiting embodiment, below the perimeter ring 10p is provided a slit that substantially develops along at least part of, preferably all, the perimeter of the auxiliary dispenser 10w.

In use, during the motion of the support 30 between the first and second position, the extraction finger 18s pushes the support 30 through the slit and causes it to arrive in correspondence of the second position 17, where there is the collection area 10r'.

The rotation of the auxiliary dispenser 10w takes place after the step of movement of the at least one first support 30 from the first position 16 in correspondence of the container 20 towards the second extracted position 17, which is therefore in correspondence of the collection area 10r' on the auxiliary dispenser 10w.

Therefore, the device 1 may be configured and programmed to cause that after the movement of the support 30, a step of transportation of the at least one first support 30 from the dispenser 10 towards a culture plate 40 takes place. There is a step of actuation of the collector 19 to collect the support 30 from the second position 17, thus from a predetermined collection area 10r' on the auxiliary dispenser 10w to collect the support 30 from the auxiliary dispenser 10w and to perform a transportation by which the support 30 is transferred from the auxiliary dispenser 10 to the culture plate 40.

In particular, the device 1 is configured for depositing the plurality of supports 30 on the auxiliary dispenser 10w such that said plurality of supports assume a substantially aligned configuration on an imaginary circumference. Clearly, such a configuration aligned on an imaginary circumference should not be construed in a limiting manner.

The collector 19 may be configured for extracting at least part of the plurality of supports 30 arranged on the auxiliary dispenser 10w in a simultaneous manner, and for performing the step of transportation (block 1004) of the plurality of supports from the auxiliary dispenser 10w toward the culture plate 40 in a single operation of movement. Thus, in one embodiment, the collector 19 collects two or more, but still only a portion of, the supports 30 from the auxiliary dispenser 10w, in an alternative embodiment, the collector 19 may be configured for collecting all of the supports 30 present on the auxiliary dispenser 10w.

In this case, the collector 19 comprises a plurality of collection heads 19t, each of which has its own hole connected to a vacuum pump by means, preferably, of a respective solenoid valve. Alternatively, all of the collection heads are connected to a vacuum pump by means of a single solenoid valve, common for all of the heads. Further alternatively, all collection heads are connected to the vacuum pump without solenoid valves.

The Applicant observes that the recesses defined on the ring 10*p*, each one, have a shape substantially tracing part of the external shape of the collection heads 19*t*. Although such collection heads are not visible in FIG. 14, these collection heads will preferably assume a substantially circular shape. The purpose of the ring 10*p*, and in particular of each of the recesses, may therefore also be considered defining an external guide during the last portion of substantially vertical stroke that the collection heads of the collector 19 execute before extracting the support 30, or the plurality of supports 30, from the respective collection area 10*r'*. In this way, a greater extraction accuracy of each support 30 is provided, even if the collection heads must perform a long stroke.

It should be noted that a same collector 19 may be configured for alternately collecting part or all of the supports 30 from the auxiliary dispenser 10*w*. In particular, should the collection take place with the exercise of a vacuum on the upper surface of the supports 30 arranged on the auxiliary dispenser 10*w*, it will be sufficient to selectively activate, by opening or closing the respective solenoid valve, the vacuum holder for one or more of the collection heads 19*t* of the collector 19, to cause—depending on the selection made—the collection of part of, or all, the supports 30 present on the auxiliary dispenser 10*w*. The activation of the vacuum holder takes place through the data processing unit.

Should the diameter of the auxiliary dispenser 10*w* be substantially similar to the diameter of the culture plate 40, the arrangement of the plurality of supports 30 on the auxiliary dispenser 10*w* will be the same as the one assumed by the plurality of supports 30 on the culture plate 40. Thanks to this aspect, it is possible to speed up the transfer of supports 30 on the culture plate 40, and—at the same time—simplify the structure of the collector 19.

In the latter case, the collector 19 is configured for performing a composite movement in order to transfer the plurality of supports 30 simultaneously on the auxiliary dispenser 10*w*. In the specific embodiment shown in the attached figures, said movement comprises a rotation about a substantially vertical axis and a translation substantially in turn along a substantially vertical axis in order to allow the approaching and moving away of the collector 19, in particular of the collection head 19*t* respectively to, and from, the auxiliary dispenser 10*w* or to, and from, the culture plate 40. In an alternative embodiment provided for by the Applicant but not shown in the attached figures, the collector 19 does not rotate but translates axially from a position substantially above the auxiliary dispenser 10*w* to a position substantially above the culture plate 40. For this reason, in that case the collector 19 will be configured for performing a composite movement comprising two translations along, respectively, a first and a second axis substantially inclined to each other, and in practice orthogonal, for allowing the approaching and the moving away of the device to, and from, respectively, the auxiliary dispenser 10*w* or to, and from, the culture plate 40 and for moving—horizontally—between the auxiliary dispenser 10*w* and the culture plate 40.

The Applicant observes that where on the auxiliary dispenser 10*w* the supports 30 are temporarily held by means of a vacuum, any rapid movements of the auxiliary dispenser 10*w*—in particular rotational and/or translational movements—can be performed without fear of undue displacement of one or more supports.

Figure 13:
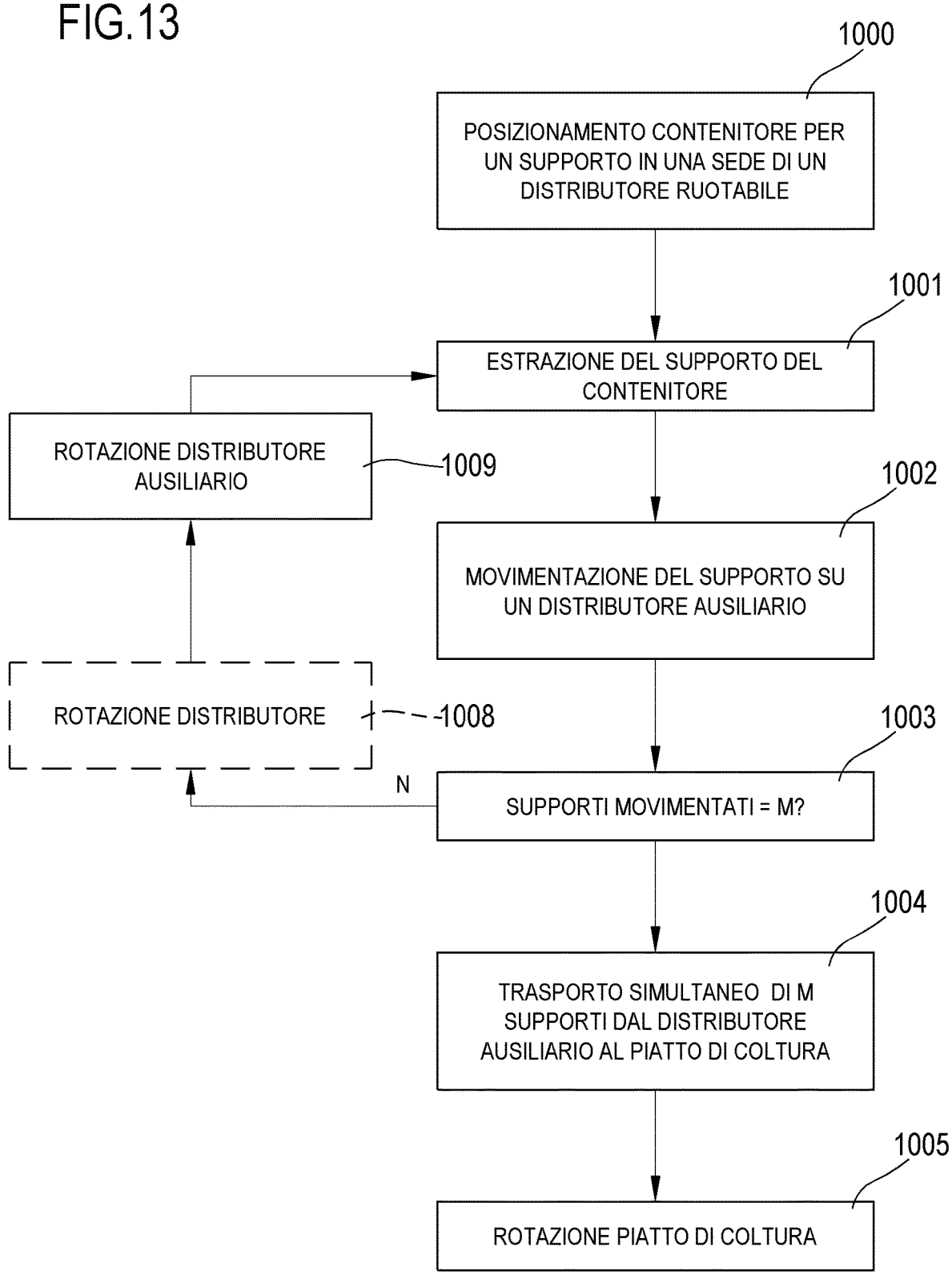
FIG. 13 shows a flow chart of a method for the distribution of impregnated supports realized by the device in the embodiment of FIG. 12.

The block diagram of FIG. 13 shows a specific embodiment of the method performed by the device of FIG. 12.

The block 1000 identifies the positioning of at least a first container 20, containing a plurality of supports 30 arranged in a stack, in a first seat 11 of a rotatable dispenser 10. If the dispenser 10 possesses a plurality of seats 11 as in the case of the non-limiting embodiment shown in Figures from 6 to 9, further steps of positioning of a second, or more, container(s) into a respective seat 11 of the dispenser 10 will be present.

After a filling—partial or total—of the seats 11 with a respective container has been completed, a step of extraction of at least one support 30 from one of the containers 20 present in the dispenser 10 may take place. Such a step of extraction is schematically represented by the block 1001.

The extraction of the support 30 firstly comprises the activation of the extractor 18 and comprises, after said activation, a movement of the support 30 between the first position 16 and the second position 17. The movement is represented by the block 1002 of the diagram of FIG. 13. In particular, in a first configuration, the dispenser 10 is positioned in a first position from which a support 30 is extracted from a first container 20 and is extracted by means of the extraction finger 18*s* from the first container 20 and is pushed into a first collection area 10*r'* of the auxiliary dispenser 10*w*.

The block diagram of FIG. 13 identifies with M a predetermined number of supports 30, which may be equivalent to the number of collection areas 10*r* of the auxiliary dispenser 10*w*. The block 1003 identifies a step of verification of whether the number of supports 30 moved from the first position 16 to the second position 17 is equal to M.

In negative case (block 1003, output N), the auxiliary dispenser 10*w* is rotated (block 1009) by a determined angle so that a new and empty collection area 10*r'* is substantially aligned with the direction of extraction identified by the axis Z.

In particular, during the rotation of the auxiliary dispenser 10*w* a vacuum is created through the holding holes 14 so that an appropriate holding of the at least one support 30 positioned in substantial correspondence of the respective at least one collection area 10*r*, part of the surface of which is a striking surface for the support 30 can be exercised.

Before the extraction of a new support 30, the dispenser 10 is moved, in particular rotated, to align a second container 20 radially on the extraction direction identified by the axis Z.

The rotation of the dispenser 10 with respect to the auxiliary dispenser 10*w* can take place: simultaneously with the rotation of the auxiliary dispenser 10*w*, before the rotation of the auxiliary dispenser 10*w* or after the rotation of the auxiliary dispenser 10*w* (block 1008). Thus, a new support 30 is extracted from the second container 20 and is extracted through the extraction finger 18*s* from the second container 20 and is pushed into the new collection area 10*r'* of the auxiliary dispenser 10*w*.

Alternatively, in a second configuration, the dispenser 10 is positioned in a first position from which a support 30 is extracted from a first container 20, is extracted by means of the extraction finger 18*s* from the first container 20 and is pushed into a first collection area 10*r'* of the auxiliary dispenser 10*w*. Subsequently, the auxiliary dispenser 10*w* is rotated for a determined angle so that a new and empty collection area 10*r'* is substantially aligned with the extraction direction identified by the axis Z. Then, a new support 30 is extracted by means of the extraction finger 18*s* from the first container 20 and is pushed into the new collection area 10*r'* of the auxiliary dispenser 10*w*. It is observed that in this case the dispenser 10 is not moved. Therefore, it is observed that the step of rotation of the dispenser 10 is not always present at every rotation of the auxiliary dispenser 10w, and for this reason the block 1008 is represented with a dashed line.

In affirmative case (block 1003, output S), a step of transportation of the plurality of M supports 30 is performed from the auxiliary dispenser 10w toward the culture plate 40; this step of transportation is identified by the block 1004 in FIG. 13. There is a step of actuation of the collector 19 to collect the at least one support 30 from the second position and a transportation, described above, performed by said collector 19 to transfer the plurality of M supports up to the culture plate 40.

Optionally, particularly should the plurality of M supports transported on the culture plate 40 said culture plate 40 be not completely filled, a step of rotation—or more generally, movement—of the culture plate 40 (block 1005) is performed.

Thanks to the operational flexibility offered by the embodiment of the device 1 wherein the auxiliary dispenser 10w is present, and assuming that different containers contain, each one, a plurality of supports 30 impregnated with a first antibiotic (first container 20) and with a second antibiotic (second container 20), it is possible to load the auxiliary dispenser 10w in an extremely efficient and easily alterable way, during two or more loading cycles, with supports 30 impregnated with the same antibiotic or with a different antibiotic.

Although this shall not intended to be limiting, the device 1 may have a movable arm 70 configured for removing and repositioning a cover on the culture plate 40. In detail, said movable arm 70 is controlled by the aforementioned data processing unit; said data processing unit may be configured or programmed to cause the covering of the culture plate 40 upon completion of the filling of said culture plate, or even only when the culture plate 40 is partially filled with supports 30.

The previously mentioned data processing unit may comprise a general-purpose processor on which a predetermined software program designed to allow the execution of the operating cycle of the device 1 described herein is executed. This program may be written in any programming language. The data processing unit may further comprise one or more ASIC-type processors configured for allowing the execution of the operating cycle of the device 1 herein described.

Further alternatively, the data processing unit may be, or comprise, a programmable logic controller (PLC). The software program may be stored in a non-transitory memory, and such memory is integrated into the data processing unit or otherwise is operationally accessible from the data processing unit through any type of connection, whether electrical, optical or wireless.

Finally, the Applicant notes that the device 1 that is the object of the present disclosure may further comprise an optical control system, configured for, and intended to, verifying the correct positioning of the supports 30 during at least part of the steps of transfer from the respective containers 20 to the culture plate 40 and further configured for verifying the presence and/or the correct positioning of the supports 30 on the auxiliary dispenser 10w. In a preferred, but non-limiting, embodiment, this optical control system is controlled, in particular at least activated and/or deactivated, through the aforementioned data processing unit.

More in detail, the optical control system comprises a camera, in particular a high-resolution camera operatively connected to a data processing unit upon which it is performed a particular software routine which allows to identify the actual presence of the at least one support 30 on the culture plate 40. This software routine is in detail initiated when the step of transportation of the at least one first support 30 towards the culture plate 40 by means of the collector is being performed, or has been completed.

The software routine may not only be able to determine whether or not the first support 30 is actually positioned on the culture plate 40, but also whether or not that support 30 is correctly positioned in a predefined position on the culture plate. In an embodiment, such a software routine, when it is detected through the camera that the support 30 has not been positioned on the culture plate 40, or in any case when it is detected through the camera that the support 30 is in a position not corresponding to said predefined position, may cause the activation of an appropriate alarm signal or, alternatively or in combination, may cause the functioning of the device 1 to stop. Additional sensor systems may be present on the device 1 to detect at least the presence or absence of a new support 30 positioned on the culture plate 40.

Alternatively or in combination with the above, the software routine may be configured for allowing to identify the shape and/or the size of the support 30. In a non-limiting embodiment, the data processing unit is configured for operatively and/or logically associating a predefined culture plate 40 with supports 30 of a predefined shape and/or size, and when in use, through the camera, it is detected that the shape and/or the size of the support 30 transported by the collector 19 on the culture plate 40 does not correspond to said predefined shape and/or size, this software routine can cause the activation of an opportune alarm signal or, alternatively or in combination, can cause the stop of the functioning of the device 1.

Still alternatively or in combination with the above, the software routine may be configured for allowing to read an identification code of the culture plate 40, for example, a barcode or an acronym or an equivalent alphanumeric code, and compare such identification code with at least one among: a type of impregnation of the support 30 (e.g., a type of antibiotic), a shape of the support 30 and/or a size of the support 30. In a non-limiting embodiment, such a comparison allows to realize said operational and/or logical association. Similarly, an operational and/or logical association can be realized between one or more containers 20, or one or more types of containers 20, and the culture plate 40, with the same functions as described above, by identifying a shape and/or size and/or a code present on one or more of the containers 20.

Although the software routine may employ several algorithms to accomplish the above-described functions, in a preferred, but not limited thereto, embodiment, it employs at least an artificial intelligence algorithm, which allows to obtain a high detection accuracy and reliability; in particular, such artificial intelligence algorithm may be based on neural networks, in particular convolutional neural networks, to perform a tagging and/or a segmentation of part of the acquired image.

Several relative positions may be assumed between the camera and the culture plate 40; one among these relative positions that wherein the camera is above the culture plate 40, for example being aligned with its axis of rotation. Another acceptable position that where the camera is at a higher height with respect to the culture plate 40 but is positioned next to it.

Where necessary, the camera can be provided with a telecentric lens, which allows to mitigate the negative effect produced by a height difference between the camera optics and the support 30 on the measurement of the shape and/or size of the support 30 itself.

It is noted then that preferably the device 1 comprises at least a vacuum switch configured for performing a measurement of a vacuum exerted by the vacuum holder and/or by the auxiliary vacuum holder 19v. Vacuum switches of known type can be suitably used in the device 1.

In a preferred embodiment the device 1 comprises a first vacuum switch for the vacuum holder operatively connected to the dispenser 10 or to the auxiliary dispenser 10w, and a second vacuum switch for the auxiliary vacuum holder 19v of the collector 19. The first vacuum switch, and when present the second vacuum switch, transmit in use a vacuum signal to the data processing unit. Such a signal is preferably an electric signal, but could also be an optical signal. The data processing unit is preferably but non-limiting thereto configured for performing an electronic comparison between the signal sent from the first vacuum switch (and/or from the second vacuum switch) with at least a vacuum threshold value. This comparison is designed to detect the correct holding of the support 30. Should the signal sent from the first vacuum switch (and/or from the second vacuum switch) indicate a vacuum value exceeding this vacuum threshold value, the action of the vacuum pump may be interrupted, or the vacuum exerted by it may be mitigated, for example through an at least partial closure of a valve, so as not to damage the support 30.

The advantages of the device and method object of the present disclosure are clear in light of the foregoing description; in details, they allow to extract in easy, flexible and rapid way a plurality of supports 30 impregnated with antibiotics for the transfer towards a culture plate 40. The extraction of the impregnated supports 30, which is performed in correspondence of the upper surface of the dispenser 10 is more easily controlled, and requires a less complex servo-actuator system. Consequently, the device 1 herein described is inherently characterized by remarkable reliability.

The device 1 herein described can be automated in an extremely effective way, achieving transfer speeds of impregnated supports 30 from the dispenser 10 to the culture plate 40 significantly faster with respect to those of competitors, in particular if the transfer speed is compared with the constructive simplification, in particular mechanical.

Studies carried out by the Applicant have shown a significant reduction of the filling time of a culture plate 40 with respect to competitors' devices; this significant reduction is in particular attested on times reduced in the order of more than half, in particular more than ⅔, of the time necessary to obtain a filling of the same culture plate 40. In a particular non-limiting embodiment, the Applicant has achieved a reduction of the time for filling the culture plate 40, going from 35" to 5".

The Applicant in particular observes that the specific embodiment of the device 1 and of the method described herein wherein the collector 19 performs a step of simultaneous transportation of a plurality of supports 30 toward the culture plate 40 allows to increment the speed of transfer of the plurality of supports toward the culture plate 40 with respect to the devices of the known art in an even more optimized way.

It is also noted that the device 1 described herein allows to be able to quickly adapt to variations in the supply chain of containers 20, and is consequently extremely flexible in use. In particular, it is noted that the particular technique of extraction of supports 30 from containers 20 accessible from an upper surface and/or however accessible upwards of the dispenser 10 allows, under determined conditions, to perform the extraction of the supports 30 from containers 20 of different type without the need for adaptation of the extractor 18. In particular, the dispenser 10, where present the auxiliary dispenser 10w, the extractor 18 and/or the collector 19 can be specifically adapted and configured for allowing a readaptation to different supports 30, the operative flexibility of the device 1 is considerably increased, and the latter can be therefore quickly put in a condition to operate with containers 20 produced by different suppliers, in particular having different sizes.

The object of the present disclosure is not limited to the embodiments shown in the attached figures; for this reason, where reference numbers are present in the following claims, such reference numbers will be provided for the sole purpose of increasing the intelligibility of the claims. Such reference numbers therefore have no limiting function.

Finally, it is clear that additions or modifications can be applied to the device and method herein described, without departing from the scope provided by the annexed claims.

The invention claimed is:

1. Method of distribution of supports impregnated with antibiotics, comprising:
   a step of positioning of a plurality of tubular containers, each one containing a plurality of supports impregnated with antibiotics and stacked in a corresponding plurality of seats of a dispenser provided with an upper surface and a lower surface opposite with respect to the upper surface, the plurality of seats being configured in such a way that respective lower ends of said tubular containers are received in the seats while respective upper ends of the tubular containers, opposite to the lower ends, are positioned in correspondence of the upper surface of the dispenser, said lower surface of said dispenser being disposed upon a supporting frame in such a way that the dispenser is movable relatively to an extractor positioned above the dispenser along a vertical axis for selectively and sequentially positioning the tubular containers in a horizontal plane for allowing the extraction of the supports from the upper ends of the tubular containers,
   a first step of extraction of at least a first support from a first container, using said extractor, the step of extraction being performed in correspondence of an upper end of the first container and comprising a movement of the first support between a first position inside the first container and a second position extracted from the first container, said first position and said second position lying in correspondence of the upper surface of the dispenser,
   a step of collection of the first support from the second position using a collector, and
   a step of transportation of the first support towards a culture plate by the collector.

2. Method according to claim 1, comprising:
   at least a second step of extraction of at least a first support from a second container by the extractor, and a step of relative movement between the extractor and the dispenser performed between said first step of extraction and said second step of extraction, or
   at least a plurality of steps of extraction of a plurality of first supports from a corresponding plurality of containers by the extractor, and a plurality of steps of relative movement between the extractor and the dispenser each one performed between two of said steps of extraction.

3. Method according to claim 1,
wherein the step of movement comprises a rotation and/or a translation of the extractor with respect to the dispenser and/or comprises a rotation and/or a translation of the dispenser with respect to the extractor.

4. Method according to claim 1,
comprising a step of positioning of the dispenser in an operating position in correspondence of which a first seat of said plurality of seats is in a predefined position of extraction configured and destined to allow the extraction of the at least a first support from an upper end of the first container housed in said first seat, by the extractor, and/or
wherein the movement of the at least a first support takes place starting from an upper end of the first container and
wherein an upper end of the first container is in correspondence of the first position, optionally said predefined position of extraction being destined to allow the extraction of the at least a first support from a supports unloading portion of the first container, from a supports unloading end of the first container directed upwards and facing itself on the upper surface of the dispenser.

5. Method according to claim 3,
wherein the step of rotation and/or translation of the dispenser comprises a step of controlled rotation of the dispenser through a rotor, so that a second seat of said plurality of seats of the dispenser is in said predefined position of extraction configured and destined to allow the extraction of the at least a first support from an upper end of a second container housed in said second seat by the extractor.

6. Method according to claim 1,
wherein the dispenser has a configuration at least partially circular and the seats are arranged according to a circular arrangement in the dispenser and
wherein the dispenser performs the steps of movement between the positions of extraction through rotation and/or
wherein the movement of the first support between the first position and the second position comprises a translation along a direction radial with respect to a center of the dispenser.

7. Method according to claim 1,
wherein the step of positioning of the plurality of containers in the corresponding plurality of seats of the dispenser comprises a positioning of a first group of containers of said plurality of containers in a first corresponding group of seats of said plurality of seats, and comprises a positioning of a second group of containers of said plurality of containers in a second corresponding group of seats of said plurality of seats,
wherein said first group of containers and said second group of containers differ by shape and/or by producer and/or
wherein said first group of seats differs in shape from said second group of seats.

8. Method according to claim 2,
comprising a step of holding of the first support of the first container by the creation of a vacuum between said upper surface of the dispenser and the first support of the first container,
wherein the step of holding comprises a holding of the first support when in correspondence of the second position and/or at the end of the step of extraction and/or before the step of transportation,
wherein the method comprises a step of holding of the first support of the second container by the creation of a vacuum between said upper surface of the dispenser and the first support of the second container, wherein the step of holding comprises a holding of the first support of the second container when in correspondence of the second position and/or at the end of the step of extraction and/or before the step of transportation, and
wherein the step of holding of the first support of the second container takes place simultaneously to the step of holding of the first support of the first container or takes place after the step of holding of the first support of the first container and after the step of controlled rotation or relative movement between the extractor and the dispenser.

9. Method according to claim 1,
wherein the movement of the first support takes place in a shaped and/or recessed position of the upper surface, said first position and said second position being positioned in said shaped and/or recessed portion.

10. Method according to claim 1, wherein said first position and said second position lie in correspondence of a same horizontal plane.

11. Device for distributing supports impregnated with antibiotics, comprising:
a supporting frame,
a dispenser, provided with an upper surface, a lower surface opposite with respect to the upper surface, and with plurality of seats configured for housing a corresponding plurality of tubular containers, each one containing a plurality of supports impregnated with antibiotics and stacked, the plurality of seats being configured in such a way that respective lower ends of said tubular containers are received in the seats while respective upper ends of the tubular containers, opposite to said lower ends of the tubular containers, are positioned in correspondence of the upper surface of the dispenser,
an extractor, configured for extracting at least a first support from an upper end of a first tubular container housed in a respective seat of the dispenser and for moving the first support between a first position inside the first container and a second position extracted from the first container, said first position and said second position lying in correspondence of said upper surface,
a collector, configured for collecting the first support from the second position and for transporting the first support from the second position towards a culture plate, and
wherein the lower surface of the dispenser is disposed upon the supporting frame in such a way that the dispenser is movable relatively to the extractor positioned above the dispenser along a vertical axis for selectively and sequentially positioning the tubular containers in a horizontal plane for allowing the extraction of the supports from the upper ends of the tubular containers.

12. Device according to claim 11,
wherein the extractor is configured for extracting at least a first support from an upper end of a second tubular container housed in a respective seat of the dispenser, and for moving the first support between a first position inside the second container and a second position extracted from the second container,
the device being configured for performing a step of relative movement between the extractor and the dispenser, performed between the extraction of the first support of the first container and the extraction of the first support of the second container, or wherein the extractor is configured for performing a plurality of steps of extraction of a plurality of first supports from a plurality of tubular containers housed in the respective seats and for moving said first supports between the first position and the second position or between respective first positions and respective second positions, lying in correspondence of an upper surface of the dispenser, and the device being configured for performing a plurality of steps of relative movement between the extractor and the dispenser, each one performed between two of said steps of extraction.

13. Device according to claim 11, wherein the extractor is configured for performing a rotation and/or translation with respect to the dispenser and/or wherein the dispenser is configured for performing a rotation and/or a translation with respect to the extractor; the device being configured for causing the rotation and/or the translation of the dispenser between two steps of extraction and/or after the transportation of the first support from the second position towards the culture plate.

14. Device according to claim 11, configured for positioning the dispenser in an operating position in correspondence of which a first seat of said plurality of seats is in a predefined position of extraction configured and destined to allow the extraction of the at least a first support from an upper end of the first container housed in said first seat, by the extractor and/or wherein the extractor is configured for moving the first support between the first position and the second position from an upper end of the first container and wherein the upper end of the first container is in correspondence of the first position, the extractor being configured for extracting the at least a first support from a supports unloading portion of the first container, from a supports unloading end of the first container directed upwards and facing itself on said upper surface of the dispenser.

15. Device according to claim 14, comprising a rotor configured for causing a controlled rotation of the dispenser so that a second seat of said plurality of seats of the dispenser is in said predefined position of extraction configured and destined to allow the extraction of the at least a first support from an upper end of a second container housed in said second seat by the extractor.

16. Device according to claim 11, wherein the dispenser has an at least partially circular configuration and the seats are arranged according to a circular arrangement in the dispenser, that is configured for rotating during the steps of movement of the dispenser between the positions of extraction and/or wherein the extractor is configured for moving the first support between the first position and the second position through a translation along a direction radial with respect to a center of the dispenser.

17. Device according to claim 11, comprising at least a first vacuum holder configured for creating a vacuum between said upper surface of the dispenser and the first support of the first container wherein the first vacuum holder is configured for holding the first support of the first container when in correspondence of the second position and/or after the movement performed by the extractor and/or before the transportation performed by said collector, the device comprising at least a second vacuum holder configured for creating a vacuum between said upper surface of the dispenser and the first support of the second container, wherein the second vacuum holder is configured for holding the first support of the second container, when in correspondence of the second position and/or after the movement performed by the extractor and/or before the transportation performed by said collector, the device being configured for activating the first vacuum holder simultaneously with the second vacuum holder, or for activating the second vacuum holder after the activation of the first vacuum holder and after the activation of a rotor.

18. Device according to claim 11, wherein the upper surface comprises a portion shaped and/or recessed and said first position and said second position are in said portion shaped and/or recessed and/or wherein the extractor is configured for moving the support within said portion shaped and/or recessed.

19. Method of distribution of supports impregnated with antibiotics, comprising:

a step of positioning of a plurality of tubular containers, each one containing a plurality of supports impregnated with antibiotics and stacked, in a corresponding plurality of seats of a dispenser provided with an upper surface and a lower surface opposite with respect to the upper surface, the plurality of seats being configured in such a way that respective lower ends of said tubular containers are received in the seats while respective upper ends of the tubular containers, opposite to the lower ends, are positioned in correspondence of the upper surface of the dispenser, said lower surface of said dispenser being disposed upon a supporting frame in such a way that the dispenser is movable relatively to an extractor positioned above the dispenser along a vertical axis for selectively and sequentially positioning the tubular containers in a horizontal plane for allowing the extraction of the supports from the upper ends tubular containers, a first step of extraction of at least a first support from a first container, using said extractor, the step of extraction being performed in correspondence of an upper end of the first container and comprising a movement of the first support between a first position inside the first container and a second position extracted from the first container, said first position and said second position lying in correspondence of the upper surface of the dispenser, a step of collection of the first support from the second position using a collector, a step of transportation of the first support towards a culture plate by the collector, and wherein said first position and said second position lie in correspondence of a surface of the dispenser accessible from above.

20. The method of claim 19, wherein the step of movement comprises a rotation and/or a translation of the extractor with respect to the dispenser and/or comprises a rotation and/or a translation of the dispenser with respect to the extractor.

21. The method of claim 20, wherein the rotation and/or translation of the dispenser comprises a step of controlled rotation of the dispenser through a rotor, so that a second seat of said plurality of seats of the dispenser is in said predefined position of extraction configured and destined to allow the extraction of the at least a first support from an upper end of a second container housed in said second seat by the extractor.

22. The method of claim 21, comprising a step of holding of the first support of the first container by the creation of a vacuum between said upper surface of the dispenser and the first support of the first container, wherein the step of holding comprises a holding of the first support when in correspondence of the second position and/or at the end of the step of extraction and/or before the step of transportation, wherein the method comprises a step of holding of the first support of the second container by the creation of a vacuum between said upper surface of the dispenser and the first support of the second container, wherein the step of holding comprises a holding of the first support of the second container when in correspondence of the second position and/or at the end of the step of extraction and/or before the step of transportation, and wherein the step of holding of the first support takes place simultaneously to the step of holding of the first support of the first container or takes place after the step of holding of the first support of the first container and after the step of controlled rotation or relative movement between the extractor and the dispenser.

\* \* \* \* \*